US011180816B2

(12) United States Patent
Alland et al.

(10) Patent No.: US 11,180,816 B2
(45) Date of Patent: Nov. 23, 2021

(54) POLYMERASE CHAIN REACTION PRIMERS AND PROBES FOR *MYCOBACTERIUM TUBERCULOSIS*

(71) Applicant: Rutgers, The State University of New Jersey, New Brunswick, NJ (US)

(72) Inventors: David Alland, Bernardsville, NJ (US); Soumitesh Chakravorty, Somerset, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 15/517,042

(22) PCT Filed: Oct. 9, 2015

(86) PCT No.: PCT/US2015/054916
§ 371 (c)(1),
(2) Date: Apr. 5, 2017

(87) PCT Pub. No.: WO2016/057905
PCT Pub. Date: Apr. 14, 2016

(65) Prior Publication Data
US 2017/0247747 A1 Aug. 31, 2017

Related U.S. Application Data

(60) Provisional application No. 62/062,351, filed on Oct. 10, 2014.

(51) Int. Cl.
*C12Q 1/689* (2018.01)
*C12Q 1/686* (2018.01)
*C12Q 1/6865* (2018.01)
*G01N 33/50* (2006.01)

(52) U.S. Cl.
CPC .............. *C12Q 1/689* (2013.01); *C12Q 1/686* (2013.01); *C12Q 1/6865* (2013.01); *G01N 33/5008* (2013.01); *C12Q 2525/143* (2013.01); *C12Q 2525/185* (2013.01); *C12Q 2600/112* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 5,541,308 | A * | 7/1996 | Hogan ................. | C12Q 1/6811 536/23.1 |
| 5,652,106 | A | 7/1997 | Plikaytis et al. | |
| 6,225,067 | B1 * | 5/2001 | Rogers ............ | G01N 35/00584 435/6.11 |
| 6,277,607 | B1 | 8/2001 | Tyagi et al. | |
| 2013/0095489 | A1 | 4/2013 | Posey et al. | |
| 2013/0130235 | A1 * | 5/2013 | Jagannath .............. | C12Q 1/701 435/5 |
| 2013/0244887 | A1 | 9/2013 | Tam et al. | |
| 2014/0004513 | A1 | 1/2014 | Wangh et al. | |

FOREIGN PATENT DOCUMENTS

| CN | 1311435 A | 9/2001 |
| CN | 1351176 A | 5/2002 |
| CN | 101168767 A | 4/2008 |
| CN | 101580879 A | 11/2009 |
| CN | 102149822 A | 8/2011 |
| CN | 102559916 A | 7/2012 |
| CN | 103045716 A | 4/2013 |
| EP | 1076099 A2 | 2/2001 |
| EP | 1713934 B1 | 3/2011 |
| JP | 2003-500038 A | 1/2003 |
| JP | 2014057572 A | 4/2014 |
| KR | 20120000868 A | 1/2012 |
| RU | 127074 U1 | 4/2013 |
| WO | 1995033851 A2 | 12/1995 |
| WO | 2000071562 A1 | 11/2000 |
| WO | 2004061134 A1 | 7/2004 |
| WO | 2013155189 A1 | 10/2013 |

OTHER PUBLICATIONS

Diffenbach (PCR methods and Applications (1993) vol. 3, pp. S30-S37) (Year: 1993).*
Roux et al(PCR Methods and Applications (1995) vol. 4, pp. s185-s194) (Year: 1995).*
Chakravony et al., "Rapid Detection of Fluoroquinolone-Resistant and Heteroresistant *Mycobacterium tuberculosis* by Use of Sloppy Molecular Beacons and Dual Melting-Temperature Codes in a Real-Time PCR Assay," Journal of Clinical Microbiology (Mar. 1, 2011); 49(3):932-940.
Chakravorty, et al: "Rapid Detection of Fluoroquinolone-Resistant and Heteroresistant *Mycobacterium tuberculosis* by Use of Sloppy Molecular Beacons and Dual Melting-Temperature Codes in a Real-Time PCR Assay", Journal of Clinical Microbiology, Mar. 2011, pp. 932-940; doi.10.1128/JCM.02271-10.
McCammon et al. "Detection of rpoB mutations associated with rifampin resistance in Mycobacterium tuberculosis using denaturing gradient gel electrophoresis", Antimicrob Agents Chemother. Jun. 2005; 49(6): 2200-9. PMID 15917513; PMCID: PMC1140537.
Li et al. "Real-time PCR and high-resolution melt analysis for rapid detection of Mycobacterium leprae drug resistance mutations and strain types", J Clin Microbiol. 2012; 50(3): 742-753. Doi: 10.1128/JCM.05183-11.
Antonova et al., "Detection of Mutations in Mycobacterium tuberculosis Genome Determining Resistance to Fluoroquinolones by Hybridization on Biological Microchips", Bulletin of Experimental Biology and Medicine, 2008, vol. 145, pp. 108-113.

(Continued)

*Primary Examiner* — Katherine D Salmon
(74) *Attorney, Agent, or Firm* — Fox Rothschild LLP

(57) ABSTRACT

The present invention relates to novel primers and sloppy molecular beacon and molecular beacon probes for amplifying segments from different genes in *Mycobacterium tuberculosis* for identifying the presence of M.tb DNA and/or resistance to anti-tuberculosis drugs.

8 Claims, 3 Drawing Sheets

Specification includes a Sequence Listing.

(56) References Cited

OTHER PUBLICATIONS

Liu, et al.: "Triplex Real-Time PCR Melting Curve Analysis for Detecting Mycobacterium Tuberculosis Mutations Associated with Resistance to Second-Line Drugs in a Single Reaction", Journal of Antimicrobial Chemotherapy, 2013, vol. 68, No. 5, pp. 1097-1103.
Ferro, et al.: "Predictive Value of Molecular Drug Resistance Testing of Mycobacterium Tuberculosis Isolates in Valle del Cauca, Colombia", Journal of Clinical Microbiology, 2013, vol. 51, No. 7, pp. 2220-2224.
Wu, Qinxue, "Molecular Mechanism and Detection of Mycobacterial Resistance" China Union Medical Univeristy Press, Dec. 31, 2012, pp. 309-312.

* cited by examiner

Figures 2A-C

SEQUENCE LISTING

<160> NUMBER OF SEQ ID NOS: 73

<210> SEQ ID NO 1
<211> LENGTH: 19
<212> TYPE: DNA
<213> ORGANISM: Artificial Sequence
<220> FEATURE:
<223> OTHER INFORMATION: synthesized oligo

<400> SEQUENCE: 1
ccggtcggtt gccgagacc                                                    19

<210> SEQ ID NO 2
<211> LENGTH: 22
<212> TYPE: DNA
<213> ORGANISM: Artificial Sequence
<220> FEATURE:
<223> OTHER INFORMATION: synthesized oligo

<400> SEQUENCE: 2
cggtcggttg ccgagaccat gg                                                22

<210> SEQ ID NO 3
<211> LENGTH: 22
<212> TYPE: DNA
<213> ORGANISM: Artificial Sequence
<220> FEATURE:
<223> OTHER INFORMATION: synthesized oligo

<400> SEQUENCE: 3
gtcggttgcc gagaccatgg gc                                                22

<210> SEQ ID NO 4
<211> LENGTH: 21
<212> TYPE: DNA
<213> ORGANISM: Artificial Sequence
<220> FEATURE:
<223> OTHER INFORMATION: synthesized oligo

<400> SEQUENCE: 4
agcgggtagc gcagcgacca g                                                 21

<210> SEQ ID NO 5
<211> LENGTH: 22
<212> TYPE: DNA
<213> ORGANISM: Artificial Sequence
<220> FEATURE:
<223> OTHER INFORMATION: synthesized oligo

<400> SEQUENCE: 5
cgggtagcgc agcgaccagg gc                                                22

<210> SEQ ID NO 6
<211> LENGTH: 23
<212> TYPE: DNA
<213> ORGANISM: Artificial Sequence
<220> FEATURE:
<223> OTHER INFORMATION: synthesized oligo

<400> SEQUENCE: 6
ccagcgggta gcgcagcgac cag                                               23

<210> SEQ ID NO 7
<211> LENGTH: 20
<212> TYPE: DNA
<213> ORGANISM: Artificial Sequence

```
<220> FEATURE:
<223> OTHER INFORMATION: synthesized oligo

<400> SEQUENCE: 7
gctggagcag atgggcttgg                                              20

<210> SEQ ID NO 8
<211> LENGTH: 22
<212> TYPE: DNA
<213> ORGANISM: Artificial Sequence
<220> FEATURE:
<223> OTHER INFORMATION: synthesized oligo

<400> SEQUENCE: 8
ccgctggagc agatgggctt gg                                           22

<210> SEQ ID NO 9
<211> LENGTH: 25
<212> TYPE: DNA
<213> ORGANISM: Artificial Sequence
<220> FEATURE:
<223> OTHER INFORMATION: synthesized oligo

<400> SEQUENCE: 9
ggctggaaga gctcgtatgg caccg                                        25

<210> SEQ ID NO 10
<211> LENGTH: 26
<212> TYPE: DNA
<213> ORGANISM: Artificial Sequence
<220> FEATURE:
<223> OTHER INFORMATION: synthesized oligo

<400> SEQUENCE: 10
gtcccatttc gtcgggtgt tcgtcc                                        26

<210> SEQ ID NO 11
<211> LENGTH: 27
<212> TYPE: DNA
<213> ORGANISM: Artificial Sequence
<220> FEATURE:
<223> OTHER INFORMATION: synthesized oligo

<400> SEQUENCE: 11
ccatttcgtc ggggtgttcg tccatac                                      27

<210> SEQ ID NO 12
<211> LENGTH: 23
<212> TYPE: DNA
<213> ORGANISM: Artificial Sequence
<220> FEATURE:
<223> OTHER INFORMATION: synthesized oligo

<400> SEQUENCE: 12
cgtcgcggac ctccagcccg gca                                          23

<210> SEQ ID NO 13
<211> LENGTH: 21
<212> TYPE: DNA
<213> ORGANISM: Artificial Sequence
<220> FEATURE:
<223> OTHER INFORMATION: synthesized oligo

<400> SEQUENCE: 13
tcacgtgaca gaccgccggg c                                            21
```

<210> SEQ ID NO 14
<211> LENGTH: 23
<212> TYPE: DNA
<213> ORGANISM: Artificial Sequence
<220> FEATURE:
<223> OTHER INFORMATION: synthesized oligo

<400> SEQUENCE: 14
gctcacgtga cagaccgccg ggc                                           23

<210> SEQ ID NO 15
<211> LENGTH: 28
<212> TYPE: DNA
<213> ORGANISM: Artificial Sequence
<220> FEATURE:
<223> OTHER INFORMATION: synthesized oligo

<400> SEQUENCE: 15
gctagtaatc gcagatcagc aacgctgc                                      28

<210> SEQ ID NO 16
<211> LENGTH: 23
<212> TYPE: DNA
<213> ORGANISM: Artificial Sequence
<220> FEATURE:
<223> OTHER INFORMATION: synthesized oligo

<400> SEQUENCE: 16
cctcccgagg gttaggccac tgg                                           23

<210> SEQ ID NO 17
<211> LENGTH: 20
<212> TYPE: DNA
<213> ORGANISM: Artificial Sequence
<220> FEATURE:
<223> OTHER INFORMATION: synthesized oligo

<400> SEQUENCE: 17
ggttaggcca ctggcttcgg                                               20

<210> SEQ ID NO 18
<211> LENGTH: 23
<212> TYPE: DNA
<213> ORGANISM: Artificial Sequence
<220> FEATURE:
<223> OTHER INFORMATION: synthesized oligo

<400> SEQUENCE: 18
cacagggtca cagtcacaga atc                                           23

<210> SEQ ID NO 19
<211> LENGTH: 23
<212> TYPE: DNA
<213> ORGANISM: Artificial Sequence
<220> FEATURE:
<223> OTHER INFORMATION: synthesized oligo

<400> SEQUENCE: 19
cgtcctcggt cgggctacac agg                                           23

<210> SEQ ID NO 20
<211> LENGTH: 25
<212> TYPE: DNA
<213> ORGANISM: Artificial Sequence
<220> FEATURE:
<223> OTHER INFORMATION: synthesized oligo

```
<400> SEQUENCE: 20
cggtcgggct acacagggtc acagt                                              25

<210> SEQ ID NO 21
<211> LENGTH: 23
<212> TYPE: DNA
<213> ORGANISM: Artificial Sequence
<220> FEATURE:
<223> OTHER INFORMATION: synthesized oligo

<400> SEQUENCE: 21
cacagggtca cagtcacaga atc                                                23

<210> SEQ ID NO 22
<211> LENGTH: 25
<212> TYPE: DNA
<213> ORGANISM: Artificial Sequence
<220> FEATURE:
<223> OTHER INFORMATION: synthesized oligo

<400> SEQUENCE: 22
gcatcgcgtg atcctttgcc agaca                                              25

<210> SEQ ID NO 23
<211> LENGTH: 24
<212> TYPE: DNA
<213> ORGANISM: Artificial Sequence
<220> FEATURE:
<223> OTHER INFORMATION: synthesized oligo

<400> SEQUENCE: 23
ctcgccggtg ccagcggata tgtc                                               24

<210> SEQ ID NO 24
<211> LENGTH: 24
<212> TYPE: DNA
<213> ORGANISM: Artificial Sequence
<220> FEATURE:
<223> OTHER INFORMATION: synthesized oligo

<400> SEQUENCE: 24
cgaccgtcca gcgcccacat cttt                                               24

<210> SEQ ID NO 25
<211> LENGTH: 21
<212> TYPE: DNA
<213> ORGANISM: Artificial Sequence
<220> FEATURE:
<223> OTHER INFORMATION: synthesized oligo

<400> SEQUENCE: 25
ccgcgagggc cccgatggtt t                                                  21

<210> SEQ ID NO 26
<211> LENGTH: 23
<212> TYPE: DNA
<213> ORGANISM: Artificial Sequence
<220> FEATURE:
<223> OTHER INFORMATION: synthesized oligo

<400> SEQUENCE: 26
ggctgggctc ccggttgatg tgg                                                23

<210> SEQ ID NO 27
```

<211> LENGTH: 24
<212> TYPE: DNA
<213> ORGANISM: Artificial Sequence
<220> FEATURE:
<223> OTHER INFORMATION: synthesized oligo

<400> SEQUENCE: 27
ggctcccggt tgatgtggtc gtag                                           24

<210> SEQ ID NO 28
<211> LENGTH: 22
<212> TYPE: DNA
<213> ORGANISM: Artificial Sequence
<220> FEATURE:
<223> OTHER INFORMATION: synthesized oligo

<400> SEQUENCE: 28
tggggcgatc ggcacaccca gc                                             22

<210> SEQ ID NO 29
<211> LENGTH: 24
<212> TYPE: DNA
<213> ORGANISM: Artificial Sequence
<220> FEATURE:
<223> OTHER INFORMATION: synthesized oligo

<400> SEQUENCE: 29
atcggtggat tgcccggcaa gctg                                           24

<210> SEQ ID NO 30
<211> LENGTH: 23
<212> TYPE: DNA
<213> ORGANISM: Artificial Sequence
<220> FEATURE:
<223> OTHER INFORMATION: synthesized oligo

<400> SEQUENCE: 30
cgttccacgg atccgcgcaa gtc                                            23

<210> SEQ ID NO 31
<211> LENGTH: 22
<212> TYPE: DNA
<213> ORGANISM: Artificial Sequence
<220> FEATURE:
<223> OTHER INFORMATION: synthesized oligo

<400> SEQUENCE: 31
gctggccgat tgccgttcca cg                                             22

<210> SEQ ID NO 32
<211> LENGTH: 23
<212> TYPE: DNA
<213> ORGANISM: Artificial Sequence
<220> FEATURE:
<223> OTHER INFORMATION: synthesized oligo

<400> SEQUENCE: 32
gatcatcaat gtggagaaag cgc                                            23

<210> SEQ ID NO 33
<211> LENGTH: 25
<212> TYPE: DNA
<213> ORGANISM: Artificial Sequence
<220> FEATURE:
<223> OTHER INFORMATION: synthesized oligo

<400> SEQUENCE: 33
ctggaacatc gaatcgcgac cgctt                                        25

<210> SEQ ID NO 34
<211> LENGTH: 22
<212> TYPE: DNA
<213> ORGANISM: Artificial Sequence
<220> FEATURE:
<223> OTHER INFORMATION: synthesized oligo

<400> SEQUENCE: 34
atcgcgaccg cttttgcag aa                                            22

<210> SEQ ID NO 35
<211> LENGTH: 21
<212> TYPE: DNA
<213> ORGANISM: Artificial Sequence
<220> FEATURE:
<223> OTHER INFORMATION: synthesized oligo

<400> SEQUENCE: 35
ctgaccgacg ccgtggtgat a                                            21

<210> SEQ ID NO 36
<211> LENGTH: 27
<212> TYPE: DNA
<213> ORGANISM: Artificial Sequence
<220> FEATURE:
<223> OTHER INFORMATION: synthesized oligo

<400> SEQUENCE: 36
ggaaatagtt ggacatgtag ccggcgt                                      27

<210> SEQ ID NO 37
<211> LENGTH: 25
<212> TYPE: DNA
<213> ORGANISM: Artificial Sequence
<220> FEATURE:
<223> OTHER INFORMATION: synthesized oligo

<400> SEQUENCE: 37
cgattcgatg ttccaggcga tactt                                        25

<210> SEQ ID NO 38
<211> LENGTH: 25
<212> TYPE: DNA
<213> ORGANISM: Artificial Sequence
<220> FEATURE:
<223> OTHER INFORMATION: synthesized oligo

<400> SEQUENCE: 38
gcgcggcaag atcatcaatg tggag                                        25

<210> SEQ ID NO 39
<211> LENGTH: 23
<212> TYPE: DNA
<213> ORGANISM: Artificial Sequence
<220> FEATURE:
<223> OTHER INFORMATION: synthesized oligo

<400> SEQUENCE: 39
gatcatcaat gtggagaaag cgc                                          23

<210> SEQ ID NO 40
<211> LENGTH: 22
<212> TYPE: DNA

<213> ORGANISM: Artificial Sequence
<220> FEATURE:
<223> OTHER INFORMATION: synthesized oligo

<400> SEQUENCE: 40
gtggatcccg gtgcccagcg cc                                    22

<210> SEQ ID NO 41
<211> LENGTH: 22
<212> TYPE: DNA
<213> ORGANISM: Artificial Sequence
<220> FEATURE:
<223> OTHER INFORMATION: synthesized oligo

<400> SEQUENCE: 41
ggtgcccagc gccgtgatga tc                                    22

<210> SEQ ID NO 42
<211> LENGTH: 28
<212> TYPE: DNA
<213> ORGANISM: Artificial Sequence
<220> FEATURE:
<223> OTHER INFORMATION: synthesized oligo

<400> SEQUENCE: 42
cgttacgctc gtggacatac cgatttcg                              28

<210> SEQ ID NO 43
<211> LENGTH: 28
<212> TYPE: DNA
<213> ORGANISM: Artificial Sequence
<220> FEATURE:
<223> OTHER INFORMATION: synthesized oligo

<400> SEQUENCE: 43
ttacgctcgt ggacataccg atttcggc                              28

<210> SEQ ID NO 44
<211> LENGTH: 24
<212> TYPE: DNA
<213> ORGANISM: Artificial Sequence
<220> FEATURE:
<223> OTHER INFORMATION: synthesized oligo

<400> SEQUENCE: 44
ggactgaacg ggatacgaat gggg                                  24

<210> SEQ ID NO 45
<211> LENGTH: 24
<212> TYPE: DNA
<213> ORGANISM: Artificial Sequence
<220> FEATURE:
<223> OTHER INFORMATION: synthesized oligo

<400> SEQUENCE: 45
gtttggcccc ttcagtggct gtgg                                  24

<210> SEQ ID NO 46
<211> LENGTH: 24
<212> TYPE: DNA
<213> ORGANISM: Artificial Sequence
<220> FEATURE:
<223> OTHER INFORMATION: synthesized oligo

<400> SEQUENCE: 46
cagcccgacg ccgaatcagt tgtt                                  24

<210> SEQ ID NO 47
<211> LENGTH: 21
<212> TYPE: DNA
<213> ORGANISM: Artificial Sequence
<220> FEATURE:
<223> OTHER INFORMATION: synthesized oligo

<400> SEQUENCE: 47
ggtgcgggcg gtgtcgaggt g                                    21

<210> SEQ ID NO 48
<211> LENGTH: 21
<212> TYPE: DNA
<213> ORGANISM: Artificial Sequence
<220> FEATURE:
<223> OTHER INFORMATION: synthesized oligo

<400> SEQUENCE: 48
gccaccgcgg ggagtttgtc g                                    21

<210> SEQ ID NO 49
<211> LENGTH: 24
<212> TYPE: DNA
<213> ORGANISM: Artificial Sequence
<220> FEATURE:
<223> OTHER INFORMATION: synthesized oligo

<400> SEQUENCE: 49
atcaacatcc ggccggtggt cgcc                                 24

<210> SEQ ID NO 50
<211> LENGTH: 24
<212> TYPE: DNA
<213> ORGANISM: Artificial Sequence
<220> FEATURE:
<223> OTHER INFORMATION: synthesized oligo

<400> SEQUENCE: 50
agctccagcc cggcacgctc acgt                                 24

<210> SEQ ID NO 51
<211> LENGTH: 28
<212> TYPE: DNA
<213> ORGANISM: Artificial Sequence
<220> FEATURE:
<223> OTHER INFORMATION: synthesized oligo

<400> SEQUENCE: 51
gctagtaatc gcagatcagc aacgctgc                             28

<210> SEQ ID NO 52
<211> LENGTH: 21
<212> TYPE: DNA
<213> ORGANISM: Artificial Sequence
<220> FEATURE:
<223> OTHER INFORMATION: synthesized oligo

<400> SEQUENCE: 52
cctcccgagg gttaggccac t                                    21

<210> SEQ ID NO 53
<211> LENGTH: 24
<212> TYPE: DNA
<213> ORGANISM: Artificial Sequence
<220> FEATURE:

<223> OTHER INFORMATION: synthesized oligo

<400> SEQUENCE: 53
gcatcgcgtg atcctttgcc agac                                    24

<210> SEQ ID NO 54
<211> LENGTH: 40
<212> TYPE: DNA
<213> ORGANISM: Artificial Sequence
<220> FEATURE:
<223> OTHER INFORMATION: synthesized oligo

<400> SEQUENCE: 54
cctgcgcgca ccagggtgcc ctagatcgac gcgtcgcagg                    40

<210> SEQ ID NO 55
<211> LENGTH: 38
<212> TYPE: DNA
<213> ORGANISM: Artificial Sequence
<220> FEATURE:
<223> OTHER INFORMATION: synthesized oligo

<400> SEQUENCE: 55 ccagggtgu cgtagatcga cgcgtcgccg cgccctgg                       38

<210> SEQ ID NO 56
<211> LENGTH: 38
<212> TYPE: DNA
<213> ORGANISM: Artificial Sequence
<220> FEATURE:
<223> OTHER INFORMATION: synthesized oligo

<400> SEQUENCE: 56
ccggcgacat caatggtgct ggtgatcgcg tccgccgg                      38

<210> SEQ ID NO 57
<211> LENGTH: 43
<212> TYPE: DNA
<213> ORGANISM: Artificial Sequence
<220> FEATURE:
<223> OTHER INFORMATION: synthesized oligo

<400> SEQUENCE: 57
cgcggccgac agttggcgct tgtgggttaa ccccgacgcc gcg                43

<210> SEQ ID NO 58
<211> LENGTH: 41
<212> TYPE: DNA
<213> ORGANISM: Artificial Sequence
<220> FEATURE:
<223> OTHER INFORMATION: synthesized oligo

<400> SEQUENCE: 58
cgcgcgccgg gccccagcac caacagtcgg agcttcgcgc g                  41

<210> SEQ ID NO 59
<211> LENGTH: 35
<212> TYPE: DNA
<213> ORGANISM: Artificial Sequence
<220> FEATURE:
<223> OTHER INFORMATION: synthesized oligo

<400> SEQUENCE: 59
cacgaccgcc cgtcacgtca tgaaagtcgg tcgtg                         35

<210> SEQ ID NO 60
<211> LENGTH: 39
<212> TYPE: DNA
<213> ORGANISM: Artificial Sequence
<220> FEATURE:
<223> OTHER INFORMATION: synthesized oligo

<400> SEQUENCE: 60
agcggtcgta atattcacgt gcacctggcc gcggccgct                    39

<210> SEQ ID NO 61
<211> LENGTH: 38
<212> TYPE: DNA
<213> ORGANISM: Artificial Sequence
<220> FEATURE:
<223> OTHER INFORMATION: synthesized oligo

<400> SEQUENCE: 61
ctcgcggcat atgccacagt cggattctct gacgcgag                     38

<210> SEQ ID NO 62
<211> LENGTH: 40
<212> TYPE: DNA
<213> ORGANISM: Artificial Sequence
<220> FEATURE:
<223> OTHER INFORMATION: synthesized oligo

<400> SEQUENCE: 62
caggcggtcg taatattcac gtgcacctgg ccgccgcctg                   40

<210> SEQ ID NO 63
<211> LENGTH: 38
<212> TYPE: DNA
<213> ORGANISM: Artificial Sequence
<220> FEATURE:
<223> OTHER INFORMATION: synthesized oligo

<400> SEQUENCE: 63
cgagcgtatg tagtagaagg tgactcggcc ggcgctcg                     38

<210> SEQ ID NO 64
<211> LENGTH: 43
<212> TYPE: DNA
<213> ORGANISM: Artificial Sequence
<220> FEATURE:
<223> OTHER INFORMATION: synthesized oligo

<400> SEQUENCE: 64
acctgccgcg gcgagacgat aggutgtagg ggtgacggca ggt               43

<210> SEQ ID NO 65
<211> LENGTH: 53
<212> TYPE: DNA
<213> ORGANISM: Artificial Sequence
<220> FEATURE:
<223> OTHER INFORMATION: synthesized oligo

<400> SEQUENCE: 65
ccgagctgat cguctgaact tcggcgtuct ttagcacccg gtugatagct cgg    53

<210> SEQ ID NO 66
<211> LENGTH: 38
<212> TYPE: DNA
<213> ORGANISM: Artificial Sequence
<220> FEATURE:
<223> OTHER INFORMATION: synthesized oligo

<400> SEQUENCE: 66
caccggcgac tcgggccacg tccaggatgt agccggtg    38

<210> SEQ ID NO 67
<211> LENGTH: 34
<212> TYPE: DNA
<213> ORGANISM: Artificial Sequence
<220> FEATURE:
<223> OTHER INFORMATION: synthesized oligo

<400> SEQUENCE: 67
cgcgcaccaa tatgatcggg tactcgactg cgcg    34

<210> SEQ ID NO 68
<211> LENGTH: 36
<212> TYPE: DNA
<213> ORGANISM: Artificial Sequence
<220> FEATURE:
<223> OTHER INFORMATION: synthesized oligo

<400> SEQUENCE: 68
tcggccatca agggaatgga gttggcgcgc ggccga    36

<210> SEQ ID NO 69
<211> LENGTH: 39
<212> TYPE: DNA
<213> ORGANISM: Artificial Sequence
<220> FEATURE:
<223> OTHER INFORMATION: synthesized oligo

<400> SEQUENCE: 69
ccgcgtgggt gtcgagtcga tctgcacaca gctacgcgg    39

<210> SEQ ID NO 70
<211> LENGTH: 20
<212> TYPE: DNA
<213> ORGANISM: Artificial Sequence
<220> FEATURE:
<223> OTHER INFORMATION: synthesized oligo

<400> SEQUENCE: 70
aaacgcgcag gtcagaaaat    20

<210> SEQ ID NO 71
<211> LENGTH: 20
<212> TYPE: DNA
<213> ORGANISM: Artificial Sequence
<220> FEATURE:
<223> OTHER INFORMATION: synthesized oligo

<400> SEQUENCE: 71
cagtgtcttg gctacctcga    20

<210> SEQ ID NO 72
<211> LENGTH: 19
<212> TYPE: DNA
<213> ORGANISM: Artificial Sequence
<220> FEATURE:
<223> OTHER INFORMATION: synthesized oligo

<400> SEQUENCE: 72
gtcggtactg acagtcccc    19

<210> SEQ ID NO 73
<211> LENGTH: 19

```
<212> TYPE: DNA
<213> ORGANISM: Artificial Sequence
<220> FEATURE:
<223> OTHER INFORMATION: synthesized oligo

<400> SEQUENCE: 73
atgcaacagc atccttgcg                                                  19
```

POLYMERASE CHAIN REACTION PRIMERS AND PROBES FOR *MYCOBACTERIUM TUBERCULOSIS*

CROSS REFERENCE TO RELATED APPLICATIONS

The application is a U.S. National Phase of International Application No. PCT/US2015/054916, filed Oct. 9, 2015, which claims priority of U.S. Provisional Patent Application No. 62/062,351, filed Oct. 10, 2014, the disclosures of which are incorporated herein by reference.

GOVERNMENT INTERESTS

The invention disclosed herein was made, at least in part, with Government support under Grant NOs. U01AI082174 and R01AI080653 from the National Institutes of Health. Accordingly, the U.S. Government has certain rights in this invention.

FIELD OF THE INVENTION

This invention relates to novel primers and sloppy molecular beacon (SMB) and molecular beacon (MB) probes for amplifying and detecting segments from different genes in *Mycobacterium tuberculosis* (M.tb) for the purpose of identifying the presence of M.tb DNA and identifying resistance to anti-tuberculosis drugs.

BACKGROUND OF THE INVENTION

Tuberculosis (TB) was declared a global public emergency nearly twenty years ago (WHO Global Tuberculosis Report 2013). Although the rate of new cases of TB has been decreasing worldwide, the millennium developmental goal target of 50% disease reduction by 2015 is unlikely to be achieved (WHO Global Tuberculosis Report 2013). An increase in the incidence of multi drug resistant (MDR) and extensively drug resistant (XDR) TB is a serious threat to these reduction goals (WHO Global Tuberculosis Report 2013). MDR TB is defined as TB resistant to treatment with at least Rifampicin and Isoniazid and XDR TB is defined as MDR TB that is additionally resistant to treatment with the Fluoroquinolone class of antibiotics and the injectable drugs Amikacin, Kanamycin and Capreomycin. Patients with drug resistant TB are best identified as rapidly as possible so that appropriate infection control and treatments can be quickly initiated Boehme, C. C., et. al, 2011, Lancet 377:1495-1505.

Conventional phenotypic methods can take weeks to months to fully define the drug resistance pattern of *Mycobacterium tuberculosis* (Mtb) due to the very slow growth of this bacterium (Heifets, L., et al., J Clin Microbiol 38:1227-1230; Kim, S. J., 2005, Eur Respir J 25:564-569; and PT, K., and K. GP., 1985, Public health Mycobacteriology: A guide for level III laboratory. Center for Disease Control, U. S Department of Health and Human Services, Atltanta, Ga.). Molecular tests offer the promise of more rapid drug resistance detection. Mtb does not naturally contain drug-resistance plasmids; thus, molecular tests are directed against chromosomal DNA. Genotypic assays are relatively easy to design because the Mtb genome has a very high degree of sequence conservation. Virtually all drug-susceptible clinical Mtb isolates have identical DNA sequences in drug resistance targets, except for a few easily identified "natural polymorphisms". It follows that any deviation from wild type sequence in a drug resistance target gene indicates the presence of drug resistance to the corresponding drug. Genotypic assays are more rapid and sensitive than phenotypic assays because DNA targets may be amplified by PCR. Biohazards can be minimized by early killing of infectious organisms.

The genetic targets which account for most cases of drug resistance in TB are now well established. Real-time PCR remains the most sensitive, rapid, and robust method to detect mutations in bacteria. Virtually all other mutation detection methods including PCR-MS, microarrays, miniarrays and next generation sequencing require nucleic acid amplification as a first step in the detection process. In contrast, real-time PCR enables sample amplification, detection and analysis to all be performed in a single well. Tubes do not have to be opened, complex fluidics are unnecessary. However, no one has been able to develop a broad methodology of drug-resistance testing that is sufficiently simple and robust to be performed outside of reference laboratories. Thus there is a need for novel primers and probes for detecting M.tb and M.tb drug resistance to the most commonly used first and second line drugs

SUMMARY OF INVENTION

This invention relates to primers, probes, and related uses in detecting M.tb and M.tb drug resistance.

In one aspect, the invention provides an isolated oligonucleotide set or primer set for amplifying a portion of a *M. tuberculosis* region selected from the group consisting of rpoB gene, gyrA gene, gyrB gene, inhA promoter, rrs gene, eis promoter, embB gene, katG gene, dosR gene, IS6110 gene, IS1081 gene. The set includes a pair of forward and reverse primers specific for the portion, where each primer has a sequence that is substantially identical to an oligonucleotide sequence selected from those listed in Tables 1A and 1B below. Accordingly, each primer has a sequence that is substantially complementary to the complement of the oligonucleotide sequence selected from those listed in the tables. In some embodiments, the sequence of the primer is identical to the oligonucleotide sequence selected from those listed in Tables 1A and 1B.

In a second aspect, the invention provides an isolated nucleic acid having a sequence that is substantially identical to one selected from those listed in Table 2. In some embodiments, the nucleic acid includes the sequence of one selected from those listed in Table 2. The nucleic acid can be labeled with, e.g., a fluorophore and a quencher at its two ends respectively, or a fluorophore linked to an internal nucleotide in the probe. Examples of the fluorophores include fluorescein, cyanine 5, or TexasRed, and TAMRA. Examples of the quenchers include BHQ1, BHQ2, and DABCYL.

The invention provides a kit containing one or more of the above-described oligonucleotide set and nucleic acid. The kit can further include a DNA polymerase, extension nucleotides, and a buffer.

In a third aspect, the invention features a method for detecting drug resistance in *M. tuberculosis*. The method includes steps of amplifying a first nucleic acid target sequence with a first primer pair to generate a first amplicon, where (i) the first primer pair is specific for a portion of a region selected from the group consisting of rpoB gene, gyrA gene, gyrB gene, inhA promoter, rrs gene, eis promoter, embB gene, and katG gene and (ii) each primer has a sequence that is substantially identical to an oligonucleotide sequence selected from those listed in Tables 1A and 1B, and detecting a mutation in the first amplicon. The presence of the mutation is indicative of the drug resistance. In the method, the detecting step can be conducted by various nucleic acid detection techniques known in the art including, e.g., sequencing-based techniques and Nucleic acid or Peptide Nucleic Acid probe hybridization-based techniques.

In one embodiment, the detecting step is performed by a process comprising (i) contacting the first amplicon with a first probe specific for the mutation under conditions conducive to a hybridization to form a probe-target hybrid; (ii) conducting a melting temperature (Tm) analysis to determine a test Tm value for the probe-target hybrid; and (iii) comparing the test Tm value with a pre-determined reference Tm value. The test Tm value, if different from the pre-determined Tm value, indicates the presence of the mutation. For example, a shift in the test Tm value of at least 3 (e.g., 3, 4, or 5) standard deviations away from the reference Tm value indicates the presence of the mutation. Conversely, a shift in the test Tm value of less than 3 standard deviations away from the reference Tm value indicates the absence of the mutation. As disclosed herein, the pre-determined reference Tm value can be the mean wild type Tm values. In one example, the test Tm value, if lower than the pre-determined reference Tm value by e.g., at least 3 standard deviations, indicates the presence of the mutation. Otherwise, the test Tm value, if not lower than the pre-determined reference Tm value by e.g., 3 standard deviations, indicates the absence of the mutation.

The method can further include amplifying a second nucleic acid target sequence with a second primer pair to generate a second amplicon, the second primer pair being specific for a portion of a second region selected from the group consisting of rpoB gene, gyrA gene, gyrB gene, inhA promoter, rrs gene, eis promoter, embB gene, and katG gene. In some embodiments, the first region is the rrs gene or the eis promoter. For example, the first region can be the rrs gene and the second region can be the eis promoter. The two regions can be amplified independently or amplified in the same reaction system using techniques such as nested PCR. In that case, the mutation can be an A1401G or C1402T mutation in the rrs gene. The mutation can be within the eis promoter region queried by the eis primer sequences.

The above-described method allows one to detect resistance to a drug selected from the group consisting of isoniazid, rifampicin, amikacin, kanamycin, capreomycin, ethambutol, and the fluoroquinolone class of drugs. The primer pair can be one selected from those listed in Tables 1A and 1B. The probe can have a sequence that is substantially identical to or completely identical to one selected from those listed in Table 2.

In a fourth aspect, the invention provides a method for detecting presence of *M. tuberculosis* in a test sample, for example, from a subject. The method includes contacting the test sample with a first primer pair under conditions conducive to an amplifying reaction to yield a first amplicon, and detecting the presence of the amplicon thereby detecting presence of *Mycobacterium tuberculosis* in the test sample. The first primer pair can be an oligonucleotide set for amplifying a portion of a *M. tuberculosis* region selected from the group consisting of gyrB gene, inhA promoter, eis promoter, embB gene, katG gene, dosR gene, IS6110 gene, IS1081 gene. Each primer of the first primer pair has a sequence that can be substantially identical to an oligonucleotide sequence selected from those listed in Table 1B. The method can further include contacting the test sample or the amplicon generated by the first primer pair with a second primer pair under conditions conducive to an amplifying reaction to yield a second amplicon, and detecting the presence of the second amplicon. In that case, presence of both the first amplicon and second amplicon indicates the presence of *Mycobacterium tuberculosis* in the test sample.

In a fifth aspect, the invention provides another method for detecting presence of *M. tuberculosis* in a test sample. The method includes contacting the test sample with a first molecular beacon probe under conditions conducive to a hybridization reaction to yield a probe-target hybrid, and detecting the presence of the probe-target hybrid thereby detecting presence of *Mycobacterium tuberculosis* in the test sample. In this method, the first molecular beacon probe has a sequence that is substantially identical to one selected from those listed in Table 2. In an example, the first molecular beacon probe is selected from the group consisting of the IS1081, dosR2, and IS6110 probe (SEQ ID No. 67-69).

The details of one or more embodiments of the invention are set forth in the description below. Other features, objectives, and advantages of the invention will be apparent from the description and from the claims.

DETAILED DESCRIPTION OF THE INVENTION

Figure 1:
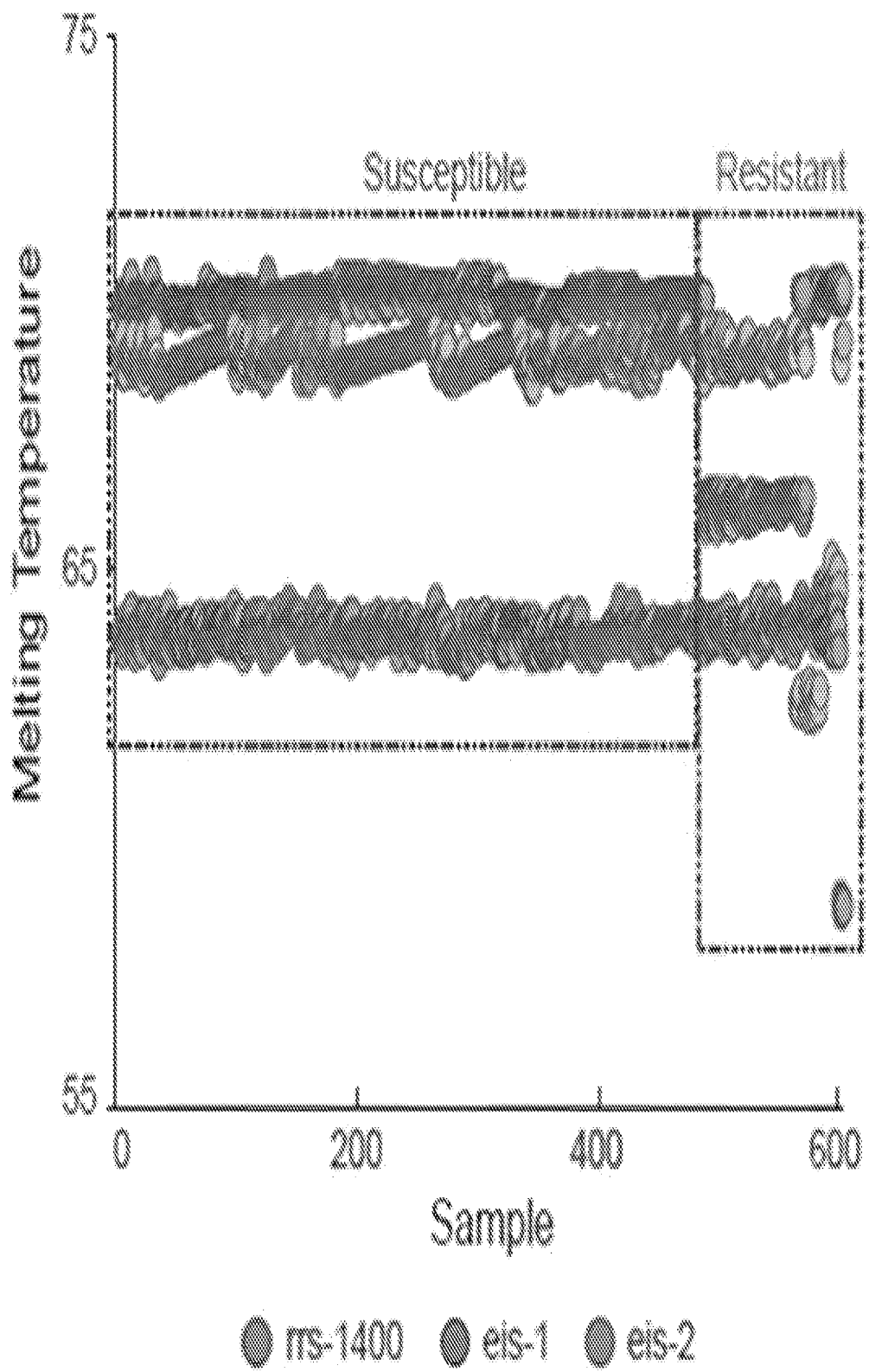
FIG. 1 is a diagram showing detection of AMK and/or KAN resistance in 603 clinical DNA samples using SMB-probe generated three-point Tm profile. Each of the three assay SMBs were tested against all M. tb DNA samples in a multiplex PCR reaction. The results for each sample are shown as a three point Tm plot on the X axis, with the Tm value of each SMB indicated on the Y axis. Isolates are sorted from left to right as phenotypically susceptible and then as resistant. Distinct Tm shifts from at least one of the three probes can be seen in each resistant isolate.

This invention is based, at least in part, on an unexpected discovery of novel primers, SMB probes, and MB probes for amplifying segments from eleven different genes in M.tb for identifying the presence of M.tb DNA and resistance to anti-tuberculosis drugs such as isoniazid, rifampicin, amikacin, kanamycin, capreomycin, ethambutol, and the fluoroquinolone class of drugs.

Primers and Probes

The primers described here amplifying the rpoB, gyrA, gyrB, inhA promoter region, rrs, eis promoter region, embB and katG genes allows sensitive amplification of drug resistance inducing mutation hotspots in M.tb. The corresponding SMB probes target and identify these mutations which result in drug resistance to the most commonly used first and second line drugs. These primers can be used with very high efficiency in both symmetric and asymmetric PCR assays. The primer and probe sequences described here have been used by the inventors to develop rapid and accurate molecular drug susceptibility testing assays for M.tb. Apart from their obvious utility in molecular diagnostic assay for M.tb, these primers will also find use for sequencing the target genes to identify the resistance inducing mutations in surveillance assays and any other probe based assays which aims at specific and sensitive identification of the common drug resistance inducing mutations in M.tb. Primer sequences amplifying the dosR, IS6110 and IS1081 genes allow highly sensitive and specific identification of M.tb and can be used in any PCR assay format aimed at highly specific and sensitive molecular diagnosis of Tuberculosis. Listed in the tables below are exemplary primers and probes of this invention.

TABLE 1A

| Primer # | SEQ ID No. | Primer name | Primer Sequence | Target Gene Portion |
|---|---|---|---|---|
| #1 | 1 | gyrA-F | CCGGTCGGTTGCCGAGACC | gyrA |
| #2 | 2 | gyrA-asym-F | CGGTCGGTTGCCGAGACCATGG | |
| #3 | 3 | P2-gyrA-nested-F | GTCGGTTGCCGAGACCATGGGC | |
| #4 | 4 | gyrA-P1-R | AGCGGGTAGCGCAGCGACCAG | |
| #5 | 5 | P2-gyrA-nested-R | CGGGTAGCGCAGCGACCAGGGC | |
| #6 | 6 | gyrA-R | CCAGCGGGTAGCGCAGCGACCAG | |
| #12 | 12 | rpo-R0 | CGTCGCGGACCTCCAGCCCGGCA | rpo B |
| #13 | 13 | rpo-R2a | TCACGTGACAGACCGCCGGGC | |
| #14 | 14 | rpo-R2b | GCTCACGTGACAGACCGCCGGGC | |
| #49 | 49 | rpoB-iF | ATCAACATCCGGCCGGTGGTCGCC | |
| #50 | 50 | rpoB-R | AGCTCCAGCCCGGCACGCTCACGT | |
| #15 | 15 | rrs-F | GCTAGTAATCGCAGATCAGCAACGCTGC | rrs |
| #16 | 16 | rrs-R | CCTCCCGAGGGTTAGGCCACTGG | |
| #17 | 17 | P3-AMG-R | GGTTAGGCCACTGGCTTCGG | |
| #51 | 51 | AMG-F | GCTAGTAATCGCAGATCAGCAACGCTGC | |
| #52 | 52 | AMG-R | CCTCCCGAGGGTTAGGCCACT | |

TABLE 1B

| Primer # | SEQ ID No. | Primer name | Primer Sequence | Target Gene Portion |
|---|---|---|---|---|
| #7 | 7 | katG-F | GCTGGAGCAGATGGGCTTGG | katG |
| #8 | 8 | P1-katG-F | CCGCTGGAGCAGATGGGCTTGG | |
| #9 | 9 | P2-katG-F | GGCTGGAAGAGCTCGTATGGCACCG | |
| #10 | 10 | katG-asym-R | GTCCCATTTCGTCGGGGTGTTCGTCC | |
| #11 | 11 | P2-katG-R2 | CCATTTCGTCGGGGTGTTCGTCCATAC | |
| #18 | 18 | eis-F | CACAGGGTCACAGTCACAGAATC | eis |
| #19 | 19 | P1-eis-F | CGTCCTCGGTCGGGCTACACAGG | |
| #20 | 20 | P2-eis-nested-F | CGGTCGGGCTACACAGGGTCACAGT | |
| #21 | 21 | P3-eis-inner-F | CACAGGGTCACAGTCACAGAATC | |
| #22 | 22 | eis-R | GCATCGCGTGATCCTTTGCCAGACA | |
| #53 | 53 | eis-R1 | GCATCGCGTGATCCTTTGCCAGAC | |
| #23 | 23 | dosR-F | CTCGCCGGTGCCAGCGGATATGTC | dosR |
| #24 | 24 | dosR-R | CGACCGTCCAGCGCCCACATCTTT | |
| #25 | 25 | IS6110-F | CCGCGAGGGCCCCGATGGTTT | IS6110 |
| #26 | 26 | IS6110-R | GGCTGGGCTCCCGGTTGATGTGG | |
| #27 | 27 | IS-SPADE R | GGCTCCCGGTTGATGTGGTCGTAG | |
| #28 | 28 | ISBcnSA-iR | TGGGGCGATCGGCACACCCAGC | |
| #29 | 29 | gyrB1-F | ATCGGTGGATTGCCCGGCAAGCTG | gyrB |
| #30 | 30 | P2-gyrB1-nested F | CGTTCCACGGATCCGCGCAAGTC | |
| #31 | 31 | P1-gyrB1-F | GCTGGCCGATTGCCGTTCCACG | |
| #32 | 32 | P3-gyrB-inner-F | GATCATCAATGTGGAGAAAGCGC | |
| #33 | 33 | P2-gyrB1-R2 | CTGGAACATCGAATCGCGACCGCTT | |
| #34 | 34 | gyrB1-R | ATCGCGACCGCTTTTTGCAGAA | |
| #35 | 35 | embB306-F | CTGACCGACGCCGTGGTGATA | embB |
| #36 | 36 | embB306-R | GGAAATAGTTGGACATGTAGCCGGCGT | |
| #37 | 37 | gyrB2-F | CGATTCGATGTTCCAGGCGATACTT | gyrB |
| #38 | 38 | P2-gyrB2-F | GCGCGGCAAGATCATCAATGTGGAG | |
| #39 | 39 | P3-gyrB-inner-F | GATCATCAATGTGGAGAAAGCGC | |
| #40 | 40 | P1-gyrB2-outer-R | GTGGATCCCGGTGCCCAGCGCC | |
| #41 | 41 | P2-gyrB2-R2 | GGTGCCCAGCGCCGTGATGATC | |
| #42 | 42 | inhA-F | CGTTACGCTCGTGGACATACCGATTTCG | inhA |
| #43 | 43 | P2-inhA-F | TTACGCTCGTGGACATACCGATTTCGGC | |
| #44 | 44 | P1-inhA-R | GGACTGAACGGGATACGAATGGGG | |
| #45 | 45 | P2-inhA-R | GTTTGGCCCCTTCAGTGGCTGTGG | |
| #46 | 46 | IS1081-outer-F | CAGCCCGACGCCGAATCAGTTGTT | IS1081 |
| #47 | 47 | IS1081-outer-R | GGTGCGGGCGGTGTCGAGGTG | |
| #48 | 48 | IS1081-inner-R | GCCACCGCGGGGAGTTTGTCG | |

TABLE 2

| Probe # | SEQ ID No. | Probe Name | Probe Sequence | Target Gene Portion |
|---|---|---|---|---|
| #1 | 54 | gyrA-1 | CCTGCgcgcaccagggtgccctagatcgacgcgtcGCAGG | gyrA |
| #2 | 55 | gyrA-2 | CCAGGGgItgUcgtagatcgacgcgtcgccgCgCCCTGG | |
| #3 | 56 | katG | CCGGCGACATCAATGGTGCTGGTGATCGCGTCCGCCGG | katG |
| #4 | 57 | rpo3 | CGCGGCcgacagtTggcgcttgtgggtTaaccccgacGCCGCG | rpoB |
| #5 | 58 | rpo4 | CGCGCGccgggccccagcaccaacagtcggagcttCGCGCG | |
| #6 | 59 | rrs1400 | cacgACCGCCCGTCACGTCATGAAAGTCGGTcgtg | rrs |
| #7 | 60 | eis1d | agcgGTCGTAATATTCACGTGCACcTGGCCGCGGCcgct | eis |
| #8 | 61 | els2b | ctcgcGGCATATGCCACAGTCGGATTCTcTGACgcgag | promoter |
| #16 | 62 | eis1d | caggcggtcgtaatattcacgtgcacctggccgccgcctg | |
| #9 | 63 | gyrB500 | cgagcGTATGTAGTAGAAGGTGACTCGGCCGGCGctcg | gyrB |
| #10 | 64 | inhA RC | acctgccGCGGCGAGACGATAGGUTGTaGGGGTGACggcaggt | inhA promoter |
| #11 | 65 | gyrB2 | ccgagctGATCGUCTGAACTTCGGCGTUCTTTAGCACCCGGTUGATagctcgg | gyrB |
| #12 | 66 | embB306 | caccggcgactcggGccacgtccaggatgtagccggtg | embB |
| #13 | 67 | IS1081 | CgcgcaCCAATATGATCGGGTACTCGACtgcgcg | IS1081 |
| #14 | 68 | dosR2 | tcggccatcaagggaatggagttggcgcgcggccga | dosR |
| #15 | 69 | IS6110 | ccgcgtGGGTGTCGAGTCGATCTGCACACAGCTacgcgg | IS6110 |

One or more of the probe sequences in Table 2 can be made in various detection formats, such as dual labeled probes including liner probes, Taqman probes, molecular beacon probes, and sloppy molecular beacon probes. A "sloppy" probe refers to a probe that is mismatch-tolerant. Mismatch-tolerant probes hybridize with and generate detectable signal for more than one target sequence at a detection temperature in an assay, and various hybrids so formed will have different melting points. Linear, or random coil, single-stranded probes are generally mismatch tolerant. Examples of such probes are hairpin or linear probes with an internal fluorescent moiety whose level of fluorescence increases upon hybridization to one or another target strand. See, e.g., U.S. Pat. Nos. 7,662,550 and 5,925,517. US 20130095479.

Preferably, the sloppy probes are dual-labeled hairpin probes or molecular beacon probes, described in U.S. Pat. Nos. 7,662,550 and 5,925,517. These hairpin probes contain a target binding sequence flanked by a pair of arms complementary to one another. They can be DNA, RNA, or PNA, or a combination of all three nucleic acids. Furthermore, they can contain modified nucleotides and modified internucleotide linkages. They can have a first fluorophore on one arm and a second fluorophore on the other arm, wherein the absorption spectrum of the second fluorophore substantially overlaps the emission spectrum of the first fluorophore. Most preferably such hairpin probes are "molecular beacon probes" that have a fluorophore on one arm and a quencher on the other arm such that the probes are dark when free in solution. They can also be wavelength-shifting molecular beacon probes with, for example, multiple fluorophores on one arm that interact by fluorescence resonance energy transfer (FRET), and a quencher on the other arm. The target binding sequences can be, for example, 12 to 50, or 25 to 50 nucleotides in length, and the hybridizing arms can be 4 to 10 or 4 to 6 (e.g., 5 or 6) nucleotides in length. Molecular beacon probes can be tethered to primers, as described in U.S. Pat. Nos. 7,662,550 and 5,925,517 and WO 01/31062.

Sloppy molecular beacon probes thus refers to such a class of fluorescently labeled hairpin oligonucleotide hybridization probes. Such probes produce a detectable signal in a homogeneous assay, that is, without having to separate probes hybridized to target from unbound probes. By virtue of their ability to bind to more than one variants of a given target sequence, the probes can be used in assays to detect the presence of one variant of a nucleic acid sequence segment of interest from among a number of possible variants or even to detect the presence of two or more variants. The probes can therefore be used in combinations of two or more in the same assay. Because they differ in target binding sequence, their relative avidities for different variants are different. For example, a first probe may bind strongly to a wild-type sequence, moderately to a first allele, weakly to a second allele and not at all to a third allele; while a second probe may bind weakly to the wild-type sequence and the first variant, and moderately to the second variant and the third variant. Additional sloppy probes will exhibit yet different binding patterns due to their different target binding sequences. Thus, fluorescence emission spectra from combinations of sloppy probes define different microbial strains or species, as well as allelic variants/mutation of genes.

As the sloppy probes reproducibly fluoresce with variable intensities after binding to different DNA sequences, combinations can be used in, for example, simple, rapid, and sensitive nucleic acid amplification reaction assays (e.g., PCR-based assays) that identify multiple pathogens or variants in a single reaction container. It is understood, however, that the assays can be performed also on samples suspected of containing directly detectable amounts of unamplified target nucleic acids. This identification assay is based on analyzing the spectra of a set of partially hybridizing sloppy signaling probes, such as sloppy molecular beacon probes, each labeled with a fluorophore that emits light with a different wavelength optimum, to generate "signature spectra" of species-specific or variant-specific DNA sequences.

Using the probes, multiplexing can be achieved, for example, by designing a different allele-discriminating molecular beacon probe for each target and labeling each probe differentially. (See, e.g., U.S. Pat. Nos. 7,662,550 and 5,925,517, WO 01/31062, and Tyagi et al. (2000) Nature Biotechnology 18: 1191-1196). Mixtures of allele-discriminating probes, each comprising aliquots of multiple colors, extends the number of probe signatures. To that end, every molecular beacon-target hybrid with a unique melting temperature will have corresponding unique signal intensity at a defined temperature and concentration of probe and amplicon. Thus, a limited number of sloppy probes could be used as probes to identify many different possible target sequences in a real-time PCR reaction. The probes can be added to the amplification reaction mixture before, during, or after the amplification. See U.S. Pat. No. 7,662,550.

This invention further provides kits containing reagents for performing the above-described methods, including PCR and/or probe-target hybridization reactions. To that end, one or more of the reaction components, e.g., PCR primers, polymerase, and probes, for the methods disclosed herein can be supplied in the form of a kit for use. In such a kit, an appropriate amount of one or more reaction components is provided in one or more containers or held on a substrate.

The kit also contains additional materials for practicing the above-described methods. In some embodiments, the kit contains some or all of the reagents, materials for performing a method that uses primers and/or probes according to the invention. Some or all of the components of the kits can be provided in containers separate from the container(s) containing the primers and/or probes of the invention. Examples of additional components of the kits include, but are not limited to, one or more different polymerases, one or more control reagents (e.g., probes or PCR primers or control templates), and buffers for the reactions (in 1× or concentrated forms). The kit may also include one or more of the following components: supports, terminating, modifying or digestion reagents, osmolytes, and an apparatus for detection.

The reaction components used can be provided in a variety of forms. For example, the components (e.g., enzymes, probes and/or primers) can be suspended in an aqueous solution or as a freeze-dried or lyophilized powder, pellet, or bead. In the latter case, the components, when reconstituted, form a complete mixture of components for use in an assay. The kits of the invention can be provided at any suitable temperature. For example, for storage of kits containing protein components (e.g., an enzyme) in a liquid, it is preferred that they are provided and maintained below 0° C., preferably at or below −20° C., or otherwise in a frozen state.

A kit or system of this invention may contain, in an amount sufficient for at least one assay, any combination of the components described herein. In some applications, one or more reaction components may be provided in pre-measured single use amounts in individual, typically disposable, tubes or equivalent containers. With such an arrangement, a PCR reaction can be performed by adding a target nucleic acid or a sample/cell containing the target nucleic acid to the individual tubes directly. The amount of a component supplied in the kit can be any appropriate amount, and may depend on the target market to which the product is directed. The container(s) in which the components are supplied can be any conventional container that is capable of holding the supplied form, for instance, microfuge tubes, ampoules, bottles, or integral testing devices, such as fluidic devices, cartridges, lateral flow, or other similar devices.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like). The kits may further include instructions recorded in a tangible form for use of the components.

Definitions

A nucleic acid refers to a DNA molecule (for example, but not limited to, a cDNA or genomic DNA), an RNA molecule (for example, but not limited to, an mRNA), or a DNA or RNA analog. A DNA or RNA analog can be synthesized from nucleotide analogs. The nucleic acid molecule can be single-stranded or double-stranded. An "isolated" nucleic acid is a nucleic acid, the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by PCR, or a restriction fragment; and (d) a recombinant nucleotide sequence that is part of a hybrid gene, i.e., a gene encoding a fusion protein.

As used herein, the term "target nucleic acid" or "target" refers to a nucleic acid containing a target nucleic acid sequence of interest. A target nucleic acid may be single-stranded or double-stranded, and often is double-stranded DNA. A "target nucleic acid sequence," "target sequence" or "target region" means a specific sequence that comprises all or part of the sequence of a single-stranded nucleic acid. A target sequence may be within a nucleic acid template or within the genome of a cell, which may be any form of single-stranded or double-stranded nucleic acid. A template may be a purified or isolated nucleic acid, or may be non-purified or non-isolated.

"Complementary" sequences, as used herein, may include, or be formed entirely from, Watson-Crick base pairs (e.g., A-T/U and C-G), non-Watson-Crick base pairs and/or base pairs formed from non-natural and modified nucleotides, and in as far as the above requirements with respect to their ability to hybridize are fulfilled. A full complement or fully complementary may mean 100% (completely) complementary or substantially complementary base pairing between nucleotides or nucleotide analogs of nucleic acid molecules.

"Substantially complementary" means that a nucleic acid or oligonucleotide has a sequence containing at least 10 contiguous bases that are at least 80%, (e.g., 85%, 90%, 95%, 96%, 97%, 98%, 99%, and 100%) to at least 10 contiguous bases in a target nucleic acid sequence so that the nucleic acid or oligonucleotide can hybridize or anneal to the target nucleic acid sequence under, e.g., the annealing condition of a PCR reaction or probe-target hybridization condition. Complementarity between sequences may be expressed a number of base mismatches in each set of at least 10 contiguous bases being compared. The term "substantially identical" means that a first nucleic acid is at least 80%, (e.g., 85%, 90%, 95%, 96%, 97%, 98%, 99%, and 100%) complementary to a second nucleic acid so that the first nucleic acid is substantially complementary to and is capable of hybridizing to the complement of the second nucleic acid under PCR annealing or probe-target hybridization conditions.

"Hybridization" or "hybridizing" or "hybridize" or "anneal" refers to the ability of completely or partially complementary nucleic acid strands to come together under specified hybridization conditions in a parallel or preferably antiparallel orientation to form a stable double-stranded structure or region (sometimes called a "hybrid" or "duplex" or "stem") in which the two constituent strands are joined by hydrogen bonds. Although hydrogen bonds typically form between adenine and thymine or uracil (A and T or U) or cytosine and guanine (C and G), other base pairs may form (e.g., Adams et al., The Biochemistry of the Nucleic Acids, 11th ed., 1992).

A "nucleic acid duplex," "duplex," "stem," "nucleic acid hybrid" or "hybrid" refers to a stable nucleic acid structure comprising a double-stranded, hydrogen-bonded region, e.g., RNA:RNA, RNA:DNA and DNA:DNA duplex molecules and analogs thereof. Such structure may be detected by any known means, e.g., by using a labeled probe, an optically active probe-coated substrate sensitive to changes in mass at its surface (U.S. Pat. No. 6,060,237), or binding agents (U.S. Pat. No. 5,994,056).

As used herein the term "amplification" and its variants includes any process for producing multiple copies or complements of at least some portion of a polynucleotide, the polynucleotide typically being referred to as a "template." The template polynucleotide can be single stranded or double stranded. A template may be a purified or isolated nucleic acid, or may be non-purified or non-isolated. Amplification of a given template can result in the generation of a population of polynucleotide amplification products, collectively referred to as an "amplicon." The polynucleotides of the amplicon can be single stranded or double stranded, or a mixture of both. Typically, the template will include a target sequence, and the resulting amplicon will include polynucleotides having a sequence that is either substantially identical or substantially complementary to the target sequence. In some embodiments, the polynucleotides of a particular amplicon are substantially identical, or substantially complementary, to each other; alternatively, in some embodiments the polynucleotides within a given amplicon can have nucleotide sequences that vary from each other. Amplification can proceed in linear or exponential fashion, and can involve repeated and consecutive replications of a given template to form two or more amplification products. Some typical amplification reactions involve successive and repeated cycles of template-based nucleic acid synthesis, resulting in the formation of a plurality of daughter polynucleotides containing at least some portion of the nucleotide sequence of the template and sharing at least some degree of nucleotide sequence identity (or complementarity) with the template. In some embodiments, each instance of nucleic acid synthesis, which can be referred to as a "cycle" of amplification, includes creating free 3' end (e.g., by nicking one strand of a dsDNA) thereby generating a primer and primer extension steps; optionally, an additional denaturation step can also be included wherein the template is partially or completely denatured. In some embodiments, one round of amplification includes a given number of repetitions of a single cycle of amplification. For example, a round of amplification can include 5, 10, 15, 20, 25, 30, 35, 40, 50, or more repetitions of a particular cycle. In one exemplary embodiment, amplification includes any reaction wherein a particular polynucleotide template is subjected to two consecutive cycles of nucleic acid synthesis. The synthesis can include template-dependent nucleic acid synthesis.

Amplification of this invention may also include isothermal amplification. The term "isothermal" means conducting a reaction at substantially constant temperature, i.e., without varying the reaction temperature in which a nucleic acid polymerization reaction occurs. Isothermal temperatures for isothermal amplification reactions depend on the strand-displacing nucleic acid polymerase used in the reactions. Generally, the isothermal temperatures are below the melting temperature (Tm; the temperature at which half of the potentially double-stranded molecules in a mixture are in a single-stranded, denatured state) of the predominant reaction product, i.e., generally 90° C. or below, usually between about 20° C. and 75° C., and preferably between about 30° C. and 60° C., or more preferably at about 37° C.

The term "primer" or "primer oligonucleotide" refers to a strand of nucleic acid or an oligonucleotide capable of hybridizing to a template nucleic acid and acting as the initiation point for incorporating extension nucleotides according to the composition of the template nucleic acid for nucleic acid synthesis. "Extension nucleotides" refer to any nucleotides (e.g., dNTP) and analogs thereof capable of being incorporated into an extension product during amplification, i.e., DNA, RNA, or a derivative of DNA or RNA, which may include a label.

As used herein, the term "oligonucleotide" refers to a short polynucleotide, typically less than or equal to 300 nucleotides long (e.g., in the range of 5 and 150, preferably in the range of 10 to 100, more preferably in the range of 15 to 50 nucleotides in length). However, as used herein, the term is also intended to encompass longer or shorter polynucleotide chains. An "oligonucleotide" may hybridize to other polynucleotides, therefore serving as a probe for polynucleotide detection, or a primer for polynucleotide chain extension.

The term "probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled with a label such as with biotin to which a streptavidin complex may later bind.

The term "detection probe" refers to an oligonucleotide having a sequence sufficiently complementary to its target sequence to form a probe:target hybrid stable for detection under stringent hybridization conditions. A probe is typically a synthetic oligomer that may include bases complementary to sequence outside of the targeted region which do not prevent hybridization under stringent hybridization conditions to the target nucleic acid. A sequence non-complementary to the target may be a homopolymer tract (e.g., poly-A or poly-T), promoter sequence, restriction endonuclease recognition sequence, or sequence to confer desired secondary or tertiary structure (e.g., a catalytic site or hairpin structure), or a tag region which may facilitate detection and/or amplification. "Stable" or "stable for detection" means that the temperature of a reaction mixture is at least 2° C. below the melting temperature (Tm) of a nucleic acid duplex contained in the mixture, more preferably at least 5° C. below the Tm, and even more preferably at least 10° C. below the Tm.

A "label" or "reporter molecule" is chemical or biochemical moiety useful for labeling a nucleic acid (including a single nucleotide), polynucleotide, oligonucleotide, or protein ligand, e.g., amino acid or antibody. Examples include fluorescent agents, chemiluminescent agents, chromogenic agents, quenching agents, radionucleotides, enzymes, substrates, cofactors, inhibitors, magnetic particles, and other moieties known in the art. Labels or reporter molecules are capable of generating a measurable signal and may be covalently or noncovalently joined to an oligonucleotide or nucleotide (e.g., a non-natural nucleotide) or ligand.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or sub-combination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting" a target nucleic acid or a cell with one or more reaction components, such as a polymerase, a primer set or a probe, includes any or all of the following situations: (i) the target or cell is contacted with a first component of a reaction mixture to create a mixture; then other components of the reaction mixture are added in any order or combination to the mixture; and (ii) the reaction mixture is fully formed prior to mixture with the target or cell.

The term "mixture" as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable.

As used herein, the term "subject" refers to any organism having a genome, preferably, a living animal, e.g., a mammal, which has been the object of diagnosis, treatment, observation or experiment. Examples of a subject can be a human, a livestock animal (beef and dairy cattle, sheep, poultry, swine, etc.), or a companion animal (dogs, cats, horses, etc).

A "sample" as used herein means any biological fluid or tissue obtained from an organism (e.g., patient) or from components (e.g., blood) of an organism. The sample may be of any biological tissue, cell(s) or fluid. The sample may be a "clinical sample" which is a sample derived from a subject, such as a human patient or veterinary subject. Useful biological samples include, without limitation, whole blood, saliva, urine, synovial fluid, bone marrow, cerebrospinal fluid, vaginal mucus, cervical mucus, nasal secretions, sputum, semen, amniotic fluid, bronchoalveolar lavage fluid, and other cellular exudates from a patient or subject. Such samples may further be diluted with saline, buffer or a physiologically acceptable diluent. Alternatively, such samples are concentrated by conventional means. Biological samples may also include sections of tissues such as frozen sections taken for histological purposes. A biological sample may also be referred to as a "patient sample." A biological sample may also include a substantially purified or isolated protein, membrane preparation, or cell culture.

The terms "determining," "measuring," "assessing," and "assaying" are used interchangeably and include both quantitative and qualitative measurement, and include determining if a characteristic, trait, or feature is present or not. Assessing may be relative or absolute. Assessing the presence of a target includes determining the amount of the target present, as well as determining whether it is present or absent.

As used herein the term "reference" value refers to a value that statistically correlates to a particular outcome when compared to an assay result. In preferred embodiments, the reference value can be determined from statistical analysis that examines the mean of wild type values. The reference value may be a threshold score value or a cutoff score value. Typically a reference value will be a threshold above (or below) which one outcome is more probable and below which an alternative outcome is more probable.

As disclosed herein, the difference of the values is indicative of presence or absence of a pathogen (e.g., *Mycobacterium tuberculosis*) or a mutation. The phrase "difference" of the level or value refers to differences in a variable (e.g., Tm) of an analyte (e.g., a probe-target hybrid) in a sample as compared to a control or reference level or value. In one embodiment, a difference of a value or level may be a statistically significant difference between the quantities of a analyte present in a sample as compared to a control. For example, a difference may be statistically significant if the measured level of the analyte falls outside of about 1.0, 2.0, 3.0, 4.0, or 5.0 standard deviations of the mean of any control or reference group.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally refers to plus or minus 10% of the indicated number. For example, "about 10%" may indicate a range of 9% to 11%, and "about 20" may mean from 18-22. Other meanings of "about" may be apparent from the context, such as rounding off, so, for example "about 1" may also mean from 0.5 to 1.4.

Uses

Two separate SMB assays that rapidly and reliably identify the M.tb mutations that are largely responsible for Rifampin and Fluoroquinolone (FQ) resistance were recently described (Chakravorty, S., B. et al., 2011, J Clin Microbiol 49:932-940; Chakravorty, S., H., et al., 2012, J Clin Microbiol 50:2194-2202). The assays disclosed herein have the advantage of being in real-time PCR format, so that they are easy to use and not subject to amplicon cross contamination. Moreover, mutation detection has been shown to be robust and amenable to high throughput testing. The examples below present a SMB TB drug resistance detection assay system, adding assays that enable detection of resistance to AMK and KAN. The causes of discordance between the assay disclosed herein and phenotypic susceptibility testing methods were also explored. The results show that some of the most commonly used phenotypic methods can miss M.tb isolates with resistance-conferring mutations if these mutations only moderately increase minimal inhibitory concentrations (MICs) to KAN. Novel mutations in whiB7 that are associated with low level KAN resistance were also discovered.

As disclosed herein, the multiplexed SMB PCR and melt assay accurately identified mutations in the rrs gene and eis promoter associated with resistance to AMK and/or KAN. The assay did not produce false resistance calls when tested against NTMs, gram positive, and gram negative bacteria. Most cases of hetero-resistance were also detected by the assay, when present. Unlike the MTBDRsl platform, the assay can be performed in a closed real-time PCR system, and can easily be adapted to high-throughput testing as all assay steps are performed in 384-well plates. The SMB assay also avoids potential problems associated with alternative methods for mutation detection. High resolution melt curve analysis requires the ability to detect subtle variations in melt curves (Yadav, R., S., et al., 2012, J Appl Microbiol 113:856-862). Other post-PCR melt based molecular assays must detect mutations by decoding complex fluorescence contours (Rice, J. E., et al., 2012. Nucleic Acids Res 40:e164.) In contrast, the SMB assay produces clear and easily distinguishable Tm peaks and definitive Tm shifts to identify the mutations of interest. Individual Tm values can also be used to cluster samples that have the same genotype.

As disclosed herein, an assay was tested out on a panel of 603 clinical samples representing both new cases of TB as well as unresolved re-treatment cases, and evaluated the relationship of the targeted mutations with the susceptibility pattern of the clinical isolates. It was observed that 100% of the isolates with rrs A1401G mutations had a strong correlation with high level resistance to both AMK and KAN. However, eis promoter mutations resulted in only moderate to low level KAN resistance and no resistance to AMK, which is consistent with previous studies (Campbell, P. J., et al, 2011, Antimicrob Agents Chemother 55:2032-2041; Zaunbrecher, M. A., et al., 2009, Proc Natl Acad Sci USA 106:20004-20009). The study here also showed that the LJ absolute concentration method for susceptibility testing does not adequately detect moderate to low level KAN resistance. In fact, nearly two-thirds of the samples with eis promoter mutations were detected as KAN susceptible in the LJ media. However, all but one sample with eis promoter mutations were detected as KAN resistant by the MGIT method. Two such isolates contained an eis C(-12)T mutation. These mutants were also resistant to KAN when tested by MYCOTB, which showed a KAN MIC of 5 µg/ml. Previous studies have suggested that clinical isolates with C(-12)T mutations do not correlate (Zaunbrecher (2009) or correlate poorly (Campbell, 2011; Hoshide, M., L. et al., 2014, J Clin Microbiol 52:1322-1329.) with KAN resistance. These studies possibly missed the relation between this mutation and low level KAN resistance due to the testing method used to establish phenotypic susceptibility. These results suggest that MGIT or MYCOTB methods should be preferred for testing phenotypic resistance to KAN. They also highlight the power of genotypic resistance tests, such as that disclosed herein, to detect mutations which cause low level resistance and may be missed by phenotypic tests alone (Rigouts, L., M. et al., 2013, J Clin Microbiol 51:2641-2645; Sirgel, F. A., et al., 2012, Microb Drug Resist 18:193-197; and Van Deun, A., et al., 2013, J Clin Microbiol 51:2633-2640).

The study set here included one sample that was a mixture of rrs wild type and rrs C1402T mutants. This sample was susceptible to both AMK and KAN in LJ media. Isolates with C1402T mutations have been reported to be susceptible to AMK but resistant to KAN (Maus, C. E., et al., 2005, Antimicrob Agents Chemother 49:3192-3197). In this particular case, repeated susceptibility tests using LJ media showed susceptibility to KAN presumably because of the hetero-resistant nature of the sample. Here, the molecular assay served as a better predictor of potentially emerging resistance than the phenotypic assay, as the SMB assay clearly detected the presence of both the wild type and the mutant DNA types.

The incidence of rrs 1484 mutations in clinical strains with AMK or KAN resistance has been very low (Georghiou, S. B., et al., 2012, PLoS One 7:e33275) making its clinical significance debatable. A separate version of the assay which targeted the rrs 1484 codon, did not detect any mutations in any of the 603 isolates in the study as well as in an additional 259 isolates from the New Jersey-New York area, which included 33 AMK and KAN resistant isolates. The lack of any rrs 1484 mutations in this enlarged study set was confirmed by Sanger sequencing (data not shown). In light of the very low prevalence of rrs 1484 mutations, this codon is unlikely to provide much value in predicting aminoglycoside resistance. Thus, it is recommended that molecular assays for aminoglycoside resistance target only the 1401-1402 codons in the rrs gene.

It was found that 22 AMK or KAN resistant samples had wild type sequences in the rrs gene and the eis promoter region. A recent study has shown a possible association between mutations in the 5'UTR of the whiB7 and KAN resistance, by identifying a 5'UTR whiB7 mutation in a single clinical strain with unexplained KAN resistance (Reeves, A. Z., et al., 2013, Antimicrob Agents Chemother 57:1857-1865). Also described were several novel 5'UTR whiB7 mutations, as well as a deletion, that appear to be associated with KAN resistance. No suitable universal biomarkers have been identified which can account for KAN and AMK resistance in the remaining 15-20% of clinical strains with wild type rrs, eis promoter region. Samples containing wild type rrs gene and eis promoter region DNA mixed with a trace amount of mutant targets from a KAN or AMK resistant subpopulation could also account for the remaining discordances between phenotypic resistance tests and the SMB assay disclosed herein. However, expensive investigation of heteroresistance was beyond the scope of this study. Some recent studies have suggested that PPE60 and Rv3168 genes might be involved in unexplained KAN resistance (Farhat, M. R., et al., 2013. Nat Genet 45:1183-

1189; Zhang, H., et al., 2013, Nat Genet 45:1255-1260) although this remains to be verified in clinical settings.

In summary, a sensitive and specific assay is developed for detection of AMK and KAN resistance in M. tb and validated it in clinical isolates with a high prevalence of MDR and XDR TB. The results show that rrs A1401G mutations encode high level cross-resistance to both AMK and KAN, and that eis promoter mutations encode moderate to low level KAN resistance, which is consistent with previous functional genomics studies (Zaunbrecher 2009). Comparing the performance of the assay disclosed herein with three different phenotypic susceptibility testing methods in solid and liquid media revealed that low to moderate level KAN resistance caused by eis promoter mutations are largely missed by the LJ based susceptibility tests. These results strongly argue for the value of genotypic tests to detect aminoglycoside resistance, and the results demonstrate the specific utility of the SMB based assay disclosed herein.

EXAMPLES

Example 1

This example describes materials and methods used in EXAMPLES 2-7 below.
DNA Samples M.tb test samples consisted of DNA isolated from 603 sequential M.tb isolates cultured from 503 patients enrolled in a natural history study of MDR tuberculosis (NCT00341601 at clinicaltrials.gov) in the National Masan Hospital in Changwon, Republic of Korea. Two cohorts were tested. Cohort A consisted of treatment naive newly suspected TB cases (158 samples) and cohort B consisted of re-treatment TB cases (445 samples). Fresh sputum samples were collected from each patient at the onset of treatment and cultured for M.tb. In a subset of patients, repeat sputum samples were collected at the $1^{st}$, $4^{th}$ and $6^{th}$ months of treatment and also cultured for M.tb. Non-Tuberculosis Mycobacteria (NTM) and Gram-positive and Gram-negative bacteria test samples were taken from the New Jersey Medical School (NJMS) DNA repository as described previously (Chakravorty, S., 2012. J Clin Microbiol 50:2194-2202).
Phenotypic Drug Susceptibility Testing Phenotypic drug susceptibility testing was performed on all 603 isolates by the absolute concentration method on LJ media to determine the susceptibility to AMK and KAN using a critical concentrations of 40 µg/ml (the standard concentration used during 2012 when the isolates were tested) for both the antibiotics (Jnawali, H. N., 2013, Diagn Microbiol Infect Dis 76:187-196) at the International Tuberculosis Research Center (ITRC), South Korea. MICs to AMK and KAN for 173/603 samples were also evaluated using the TREK Sensititre® MYCOTB MIC plates ("MYCOTB"; TREK Diagnostic Systems, Cleveland, Ohio, USA) as described previously (Lee, J., 2014, Antimicrob Agents Chemother 58:11-18). For 560/603 samples, resistance to KAN was also evaluated using the Mycobacterial Growth Indicator Tube (MGIT) system (Becton Dickinson, Franklin Lakes, N.J., USA) at a critical concentration of 2.5 µm/ml. For the samples with phenotypic susceptibility test results that were discordant with Sanger sequencing results of the target genes, the phenotypic susceptibility tests were repeated to confirm the initial findings. In cases where MGIT and LJ susceptibility test results showed discordance, both the assays were repeated to confirm or rectify the initial findings.
DNA Preparation and Sequencing DNA for both SMB assay testing and Sanger sequencing was prepared from cultured isolates by boiling one loopful of culture in 200 µl of Instagene Matrix resin (Bio-Rad Laboratories, Hercules Calif., USA) in the presence of 0.1% Triton X100 for 10-15 minutes. The supernatant was recovered after centrifugation and quantified using a Nanodrop microvolume spectrophotometer (Thermo Fisher Scientific, Waltham, Mass., USA). For Sanger sequencing, two different fragments of the rrs gene (nucleotides 420-980 and 1293-1537) and a part of the upstream eis coding region plus the entire eis promoter were amplified using 0.5 µM of forward and reverse primers, 1×PCR buffer, 250 mM dNTPs, 2.5 mM $MgCl_2$ and 0.03 U/µl of AmpliTaq Gold DNA polymerase enzyme (Applied Biosystems, Foster City, Calif., USA) according to the following parameters: initial denaturation at 95° C. for 10 min, followed by 40 cycles of 95° C. for 10s, 58-60° C. for 30s and 72° C. for 10-30s depending on the amplicon size. The eis promoter region and the rrs gene fragments were amplified as described previously (10, 33). For a subset of samples, a 538 bp fragment from the whiB7 gene including 412 bp of the 5' untranslated region and 126 bp from the ORF was amplified and sequenced using primers whiB7F 5'aaacgcgcaggtcagaaaat 3' and whiB7R 5'cagtgtcttggctacctcga 3' (SEQ ID Nos: 70 and 71). Additionally, a 275 bp fragment from the whiB7 gene, which included almost the entire whiB7 ORF was also amplified using the primers whiB7-ingene-F 5' GTCGGTACTGACAGTCCCC 3' and whiB7-ingene-R 5'ATGCAACAGCATCCTTGCG 3'(SEQ ID Nos: 72 and 73). The PCR products were subjected to bidirectional sequencing using the gene-specific forward and reverse primers in a 3130XL Genetic Analyzer (Applied Biosystems, Foster City, Calif., USA) using a BigDye Terminator, version 3.1, cycle sequencing kit (Applied Biosystems) according to the manufacturer's instructions.
Assay Molecular Beacons and Primers The SMB assays targeted M.tb mutations in codons 1401 and 1402 of the rrs gene and mutations along the promoter region of the eis gene. A 113 bp fragment (nucleotides 1335-1451) was amplified from the rrs gene using the primers AMG-F (5'-GCTAGTAATCGCAGATCAGCAA-CGCTGC-3', SEQ ID No: 51) and AMG-R (5'-CCTCCCGAGGGTTAGGCCACT-3', SEQ ID No: 52) and a 98 bp fragment encompassing the promoter region and the initial five codons of the eis gene (nucleotides −81 to 17) was amplified using the primers eis-F (5'-CACAGGGT-CACAGTCACAGAATC-3', SEQ ID No: 18) and eis-R (5'-GCATCGCGTGATCCTTTGCCAGAC-3', SEQ ID No: 53). The rrs primers were designed to be specific to *Mycobacterium* genus and the eis primers were designed to be specific to the M.tb complex. One SMB probe rrs-1400 (5'-6carboxyfluorescein-cacgaccgcccgtcacgtcatgaaagtcgg-tcgtg-BHQ1-3', SEQ ID No: 59) and two SMB probes eis-1 (5'-Cyanine5-caggcggtcgtaatattcacgtgcacctggccgccgcctg-BHQ2-3', SEQ ID No: 16) and eis-2 (5'-TexasRed-ctcgcgg-catatgccacagtcggattctctgacgcgag-BHQ2-3 SEQ ID No: 61) (where underlined sequences represent the stem portion of the SMB and BHQ represents black hole quencher) were targeted against the rrs gene and the eis promoter region respectively. The rrs probe was designed to be complementary to the antisense strand and the eis probes were designed to be complementary to the sense strand. The SMBs were designed using the in silico DNA folding program at http:// mfold.rna.albany.edu/?q_mfold/dna-folding-form, and the probe-target hybrid folding program at http://mfold.rna.albany.edu/?q_DINAMelt/Two-state-melting was used to predict the possible probe-target hybrid structures and melting temperatures (Tms). The probes were designed to generate a maximum Tm difference between wild-type and mutant sequences in their respective target regions to enable unambiguous mutation identification. Primers were obtained from Sigma Aldrich (St. Louis, Mo., USA), and SMB probes from Biosearch Technologies (Novato, Calif., USA).

Assay Procedure

All the samples were independently coded and randomly distributed to ensure that assay validation was performed in a blinded manner. The assay was tested at both ITRC in Masan, South Korea and New Jersey Medical School (NJMS), Rutgers, Newark, N.J. Once testing of the entire 603 sample set was completed, the samples were decoded and the PCR results were compared to the corresponding sequencing, and phenotypic drug susceptibility testing results. The results obtained at each site were also compared. Assay results were not reported to the treating physicians and were not used to guide any treatment decisions. PCR was performed in 384-well plates using a Roche Light Cycler 480 II real-time PCR system (Roche Diagnostics Co. Indianapolis, Ind., USA) in 20 µl reaction volumes containing 100 nM forward primer and 1 µM reverse primer for the rrs gene and 1 µM forward primer and 50 nM reverse primer for the eis promoter region, 1 ng/µl of rrs-1400 and eis-1 probes and 0.8 ng/µl of eis-2 probe, 4 mM MgCl$_2$, 250 mM deoxynucleoside triphosphates (dNTPs), 1×PCR buffer, 8% glycerol, 0.06 U/µl of Platinum® TfiExo(-) DNA polymerase (Life Technologies, Grand Island, N.Y., USA), and 2 to 5 ng of sample DNA or an equivalent volume of water. PCR was carried out with the following steps: activation of the enzyme for 2 min at 95° C., followed by 50 cycles of denaturation at 95° C. for 10s and combined annealing and extension at 67° C. for 30s. Following PCR cycling, post-PCR-Tm analysis was performed by denaturation at 95° C. for 2 min, followed by cooling down to 45° C. and then gradual heating to 85° C., with continuous monitoring of fluorescence during the process at a rate of 1 data acquisition per degree centigrade. Tm values were identified at the end of the reaction using the Tm calling software (Light Cycler 480 software). However, each Tm was also verified by a trained observer before the final identification of the Tm value was made. Samples showing distinct double peaks for any probes corresponding to wild type and mutant Tms were considered to be indicative of hetero-resistance. A no template control using sterile water instead of DNA as the template was used as the DNA-negative control, and a DNA-positive control using 1 ng of genomic DNA from M. tb H37Rv as the template was also included in each assay plate.

Human Subjects Approvals

This study was approved by the National Masan Hospital, NIAID and Rutgers (formerly UMDNJ) institutional review boards, and all subjects gave written informed consent (Rutgers IRB protocol number 0120090104).

Example 2. Identification of Tm Values Associated with Wild Type and Mutant Sequences The SMB-based assay disclosed herein detected resistance to AMK and KAN by looking for mutations in the M.tb rrs gene and eis promoter that have known associations with resistance. The assay consisted of a PCR step followed by a Tm analysis in the presence of SMB probes complementary to portions of the rrs and eis target amplicons. The inventors first evaluated the capability of the assay to identify the target mutations on artificial oligonucleotides and sequenced DNA templates from selected wild type and mutant M.tb. strains (data not shown). Wild type sequences were identified by the presence of Tm values within 1° C. of the known mean values for wild type targets. Mutant sequences were identified by a shift in Tm values of at least five standard deviations away from the mean wild type Tm values. The ability of the assay to detect the most prevalent mutations associated with AMK and KAN resistance was then evaluated on the clinical DNA samples. Tests were performed on a panel of 603 clinical samples, consisting of 487 samples with wild type sequences and 116 samples with mutations in the assay targets. Five of these samples had mixtures of both wild type and mutant DNA detected on Sanger sequencing. The SMB assay correctly identified 115/116 (99%) mutant or mixed (heterogeneous samples containing both mutant and wild type DNA) samples as mutant or mixed and 487/487 (100%) pure wild type samples as wild type. A single mixed sample (as indicated by Sanger sequencing) was identified as a wild type sample by the assay disclosed herein. The Tm values produced by each SMB probe in the setting of wild type or mutant targets were highly reproducible. For wild type targets, probes rrs-1400, eis-1 and eis-2 showed mean Tm values of 70.1° C.±0.15, 63.9° C.±0.19 and 69° C.±0.23, respectively (Table 3). For mutant Tm targets, A1401G and C1402T, the mutations resulted in a 3.9° C. (±0.17) and 5.6° C. (±0.21) decrease in Tm values in probe rrs-1400, respectively (Table 3). Similarly, the eis-1 and the eis-2 probes robustly detected a range of mutations in the eis promoter region as mutant by developing a 4.3° C. to 6.5° C. decrease in Tm values, compared to the expected wild type Tm values (Table 3). The PCR assays performed in the two different laboratories at Rutgers and ITRC were in complete agreement for all the samples detected as wild type and mutant as well as mixtures.

The assay results enabled us to clearly segregate the 603 samples into wild type and mutant Tm cluster types based on their individual three-point Tm patterns (FIG. 1). The assay correctly identified mutations in all 75 samples that only contained the A1401G mutation (Table 3, FIG. 2. panel A). Three of the four samples containing mixtures of A1401G and wild type sequence were also detected as mixed wild type/mutant based on the presence of a double Tm peak. A single sample that contained a mixture of the C1402T mutation and wild type DNA was also identified by the presence of double Tm peaks from the sample with a mutant Tm specific for the C1402T mutation (Table 3, FIG. 2. panel A). The 32 samples with eis promoter region mutations included five different polymorphisms (at positions −8, −10, −12, −14 and −37). All of these mutations were successfully detected by either one of the eis SMBs (Table 3, FIG. 2. panels B and C). Four samples that had mutations in both the rrs gene and the eis promoter region were also correctly detected as double mutants (Table 3). Sequencing of the rrs gene did not identify any samples with a codon 1484 mutation, regardless of its drug susceptibility pattern.

Example 3. Identification of Amikacin Resistance

Figure 2:
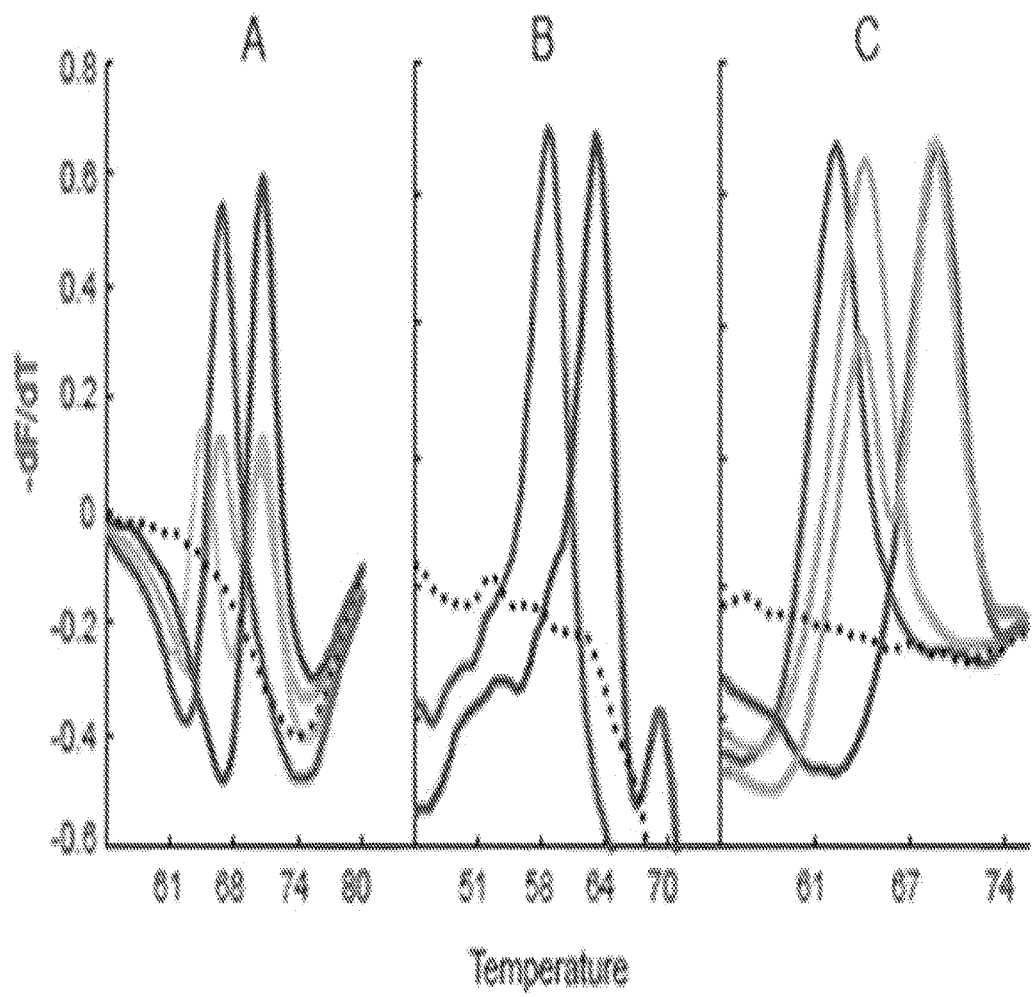
FIGS. 2A, 2B and 2C are diagrams showing first derivative melt peak profiles of three SMB probes. The melt peak profiles of wild type, mutant and mixed DNA samples are shown for the rrs-1400 SMB probe (2A), the eis1 SMB probe (2B), and the eis2 SMB probe (2C). Each melt curve represents an individual strain.

In this example, assays were performed to evaluate the performance of the molecular assay relative to phenotypic drug susceptibly test results. The apparent performance of a genotypic drug susceptibility test can vary depending on the mutations selected for inclusion in the test and the phenotypic assay that is used as a gold standard (Kim, S. J. 2005 Eur Respir J 25:564-569; Rigouts, L., et al., 2013, J Clin Microbiol 51:2641-2645; and Van Deun, A., et al., 2013, J Clin Microbiol 51:2633-2640). Considering the LJ based drug susceptibility testing method as the gold standard (performed for all the 603 study samples), the rrs SMB Tm characteristic of the A1401G mutation, classified 82/90 of the AMK resistant samples as resistant, (sensitivity of 91.1%; 95% CI, 82.8% to 96.8%). The wild type Tm classified 512/513 of the AMK susceptible samples as susceptible. A single isolate among the 513 AMK susceptible isolates was identified as a mixture of wild type and C1402T mutant DNA by the SMB assay disclosed herein due to the presence of a clear double peak generated by the rrs SMB probe, corresponding to the wild type Tm and a specific C1402T mutant Tm (FIG. 2. panel A). This was also confirmed by Sanger sequencing. Since previous studies have shown that the C1402T mutation does not code for AMK resistance (24), the specific Tm corresponding to the C1402T mutation can be considered as an indicator of AMK susceptibility. This consideration resulted in the assay disclosed herein correctly detecting all the 513/513 AMK susceptible samples resulting in a specificity of 100% (95% CI, 99 to 100%). Including Tm values characteristic for mutations in the eis promoter region in the analysis did not increase the sensitivity for detecting AMK resistance, but decreased the specificity from 100% to 93.8% (95% CI, 91.2 to 95.6%). These results are consistent with previous reports which suggest that the eis promoter mutations are not associated with AMK resistance as defined by the LJ drug susceptibility testing (Campbell 2011 and Zaunbrecher 2009).

Example 4. Identification of Kanamycin Resistance

The performance of an assay to detect KAN resistance was also evaluated using LJ based drug susceptibly testing as the gold standard for all the 603 samples. Using Tm values generated by the rrs SMB disclosed herein typical for either the A1401G or the C1402T mutation to define resistance, the assay detected 82/106 samples as KAN resistant (sensitivity 77.4%; 95% CI 68.0 to 84.7%). Conversely, using a rrs SMB Tm characteristic for wild type target to define susceptibility, identified 496/497 KAN susceptible samples as susceptible (Table 4) (specificity 99.8%; 95% CI, 98.7 to 100%). Adding Tm values of the two eis SMBs characteristic for mutations in the eis promoter region to the definition of resistance, increased the sensitivity for detecting KAN resistance from 77.4% to 87.7% (95% CI, 79.5 to 93%), as 11 additional KAN resistant samples were classified as resistant. However, specificity decreased from 99.8% to 95.6% (95% CI, 93.3 to 97.1%) as 21 KAN susceptible samples with eis promoter mutations were now "falsely" detected as KAN resistant (Table 4).

Then a similar analysis was performed using MGIT-based drug susceptibility test results as the gold standard for the 560 of the samples for which a MGIT result was available. This subset included all the samples harboring only eis promoter mutations. Comparison of the assay results to the MGIT based gold standard helped to clarify the eis mutants with discordant KAN resistance in LJ media. Using MGIT as the gold standard and only the rrs SMB Tm values characteristic for A1401G or C1402T mutations to define KAN resistance, only 63/113 KAN resistant samples were identified as resistant by the SMB assay (sensitivity 55.8%; 95% CI, 46.1 to 65%). Conversely, using the rrs SMB Tm characteristic for wild type target to define susceptibility identified 445/447 samples as KAN susceptible (specificity 99.8%; 95% CI, 98.5 to 100%; Table 4). Unlike the case with LJ based susceptibility testing, including the Tm values characteristic for eis promoter mutations in this case, increased sensitivity for resistance testing from 55.8% to 82.3% with the specificity of the assay for KAN resistance still remaining very high at 99.5% (95% CI, 98.2 to 100%). Thus, based on a MGIT-based susceptibility test, the eis assay allowed for the detection of 29 additional KAN resistant samples without affecting specificity (Table 4).

Example 5. Relationship Between Mutations Detected by the Assay and Mic

Figure 3:
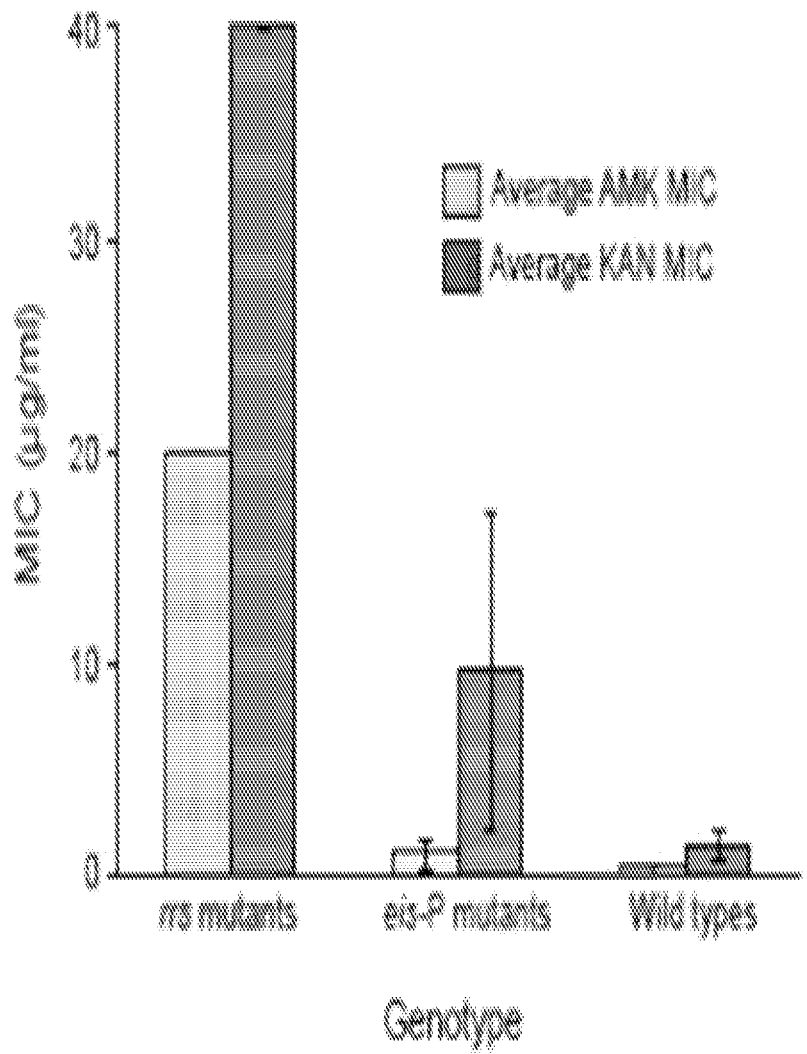
FIG. 3 is a diagram showing MIC values of rrs and eis mutant and wild type strains. The average MIC values to AMK and KAN for the rrs and the eis mutants and the wild type strains are shown. Error bars represent the ±one standard deviation of the MIC values. eis-P indicates eis gene promoter.

The discordance between resistance as defined by the assay disclosed herein and resistance as defined by two phenotypic susceptibility test methods disclosed herein principally involved isolates with eis promoter mutations. Previous studies have shown that the eis promoter mutations give rise to relatively low levels of KAN resistance, while rrs gene mutations result in high level resistance to AMK, KAN and CAP (Campbell 2011; Du, Q., et al., 2013, Diagn Microbiol Infect Dis 77:138-142; Georghiou 2012; and Zaunbrecher 2009). An additional finding in the results was the discordance between LJ versus MGIT-based susceptibility test results. MIC testing was performed to more carefully explore the relationship between rrs and eis promoter mutations, and their differential susceptibility patterns in the LJ and the MGIT system. Samples that were either susceptible to both AMK and KAN (and wild type at both the target regions), or chosen to be representative of the most common mutation types in the two target genes (rrs A1401G and eis G(-10)A, C(-14)T and G(-37)T) were tested by the MYCOTB method to determine their MIC. Additional isolates known to be wild type in both of the assay targets were also tested as controls. It was observed that the AMK MICs of the isolates that only had eis promoter mutations (without rrs mutations) ranged between 0.25 µg/ml and 2 µg/ml, with majority of samples showing MICs of 0.5 µg/ml to 1 µg/ml (FIG. 3). Only one eis promoter mutant had an AMK MIC of 4 µg/ml. Control isolates with no eis promoter or rrs mutations had MICs between 0.25 µg/ml and 0.5 µg/ml range. Thus, the AMK MICs of the isolates with either wild type or mutant eis promoter sequences overlapped substantially. In contrast, the KAN MICs for most of the same eis promoter mutants ranged from 5 µg/ml to 20 µg/ml, with one isolate showing an MIC of 40 µg/ml (FIG. 3). Only two eis promoter mutants had low MICs of 2.5 µm/ml. The isolates with wild type eis promoter sequences showed MICs between 0.6 µg/ml to 2.5 µg/ml which is 2 to 30 fold less than the mean MIC of the eis promoter mutants (FIG. 3). Thus, in contrast to the situation with AMK, the KAN MICs of the wild type isolates overlapped very little with the KAN MICs of the eis promoter mutants. These results strongly suggest that eis promoter mutants should be considered to have low to moderate level KAN resistance even if resistance is not detected on LJ based or even MGIT-based susceptibility tests.

Example 6. Assay Specificity Against Bacteria Other than M. Tb

The analytical specificity of the assay was tested against a panel of 18 species of non-tuberculous Mycobacteria (NTM) obtained from the ATCC repository (Manassas, Va., USA), 121 clinical NTM strains representing 26 species, and 18 species of gram positive and gram negative bacteria. The rrs region targeted in the assay here is highly conserved among different NTM species. Thus, the rrs assay generated a Tm of 70° C. (which is identical to the Tm generated in the presence of wild type M. tb DNA) for all the NTM tested as expected based on sequence homology expect for M. xenopi, which did not generate any Tm. The NTM species which generate Tm values identical to aminoglycoside susceptible M tb would not be expected to cause a false-resistance test result. When M tb DNA from rrs mutant AMK and KAN resistant strains was mixed with 10 to 20 fold excess of NTM DNA, a distinct double Tm peak was produced by the assay, corresponding a mutant Tm value from the M tb target and a wild type Tm value from the NTM sequence (data not shown) indicating that resistance-associated rrs mutations can be detected in M.tb by the assay here even in presence of a large background of NTM DNA. No visible melt curve was generated by the eis probes in the presence of any NTMs species tested even when $10^7$ genome equivalents of DNA were added to the PCR assay. None of the gram positive or gram negative bacteria produced Tm values to any of the rrs or eis SMBs; thus, they did not cause any false resistance calls to be made by the assay.

Example 7. Additional Genetic Causes of AMK and KAN Resistance

The study in this example included 22 samples that were resistant to AMK and/or KAN, but had wild type rrs gene and eis promoter sequences. Recent investigations have suggested that mutations in the 5' untranslated region (UTR) of the whiB7 gene may cause aminoglycoside resistance in M tb (27). To determine whether whiB7 mutations could be responsible for some of the phenotypically resistant but assay-susceptible isolates, all the 22 samples were sequenced in a 412 bp region upstream of the whiB7 gene start site plus a portion of the whiB7 open reading frame. As a control set, 30 randomly picked pan-susceptible isolates were also sequenced. Of the 22 discordant isolates, six isolates from three patients showed mutations in the whiB7 5'UTR region. One sample had a cytosine deletion at the position +138 in the 5'UTR, two samples from one patient contained an A to G mutation in the position +237, and the remaining three samples from a single patient showed an A to C mutation at position +273 (Table 5) considering the transcription start site as +1 (Reeves, A. Z., 2013, 57:1857-1865). Three samples from a single patient failed to generate any amplification from the 5'UTR after repeated PCR attempts despite functioning positive PCR controls. This suggested the presence of a large deletion in the 5'UTR region, since a 275 bp fragment could be easily amplified from within the whiB7 ORF for all the three samples. All the samples with whiB7 mutations were resistant only to KAN which is consistent with the presumed whiB7 mechanism of action by upregulation of the eis gene (Reeves 2013). The KAN MICS for these isolates were also low at 5 μg/ml, which is similar to that observed for eis promoter mutants. None of the 30 control samples that were susceptible to aminoglycosides had any mutations in the 5'UTR of the whiB7 gene. Further studies are necessary to confirm the relationship of these mutations and the deletion in the 5'UTR of the whiB7 gene with aminoglycoside resistance. However, the absence of such mutations in the susceptible strains implies that they might have some role to play in aminoglycoside resistance and future assays could target these mutations to improve sensitivity for detecting low-level KAN resistance.

TABLE 3

Melting temperature (Tm) values of the rrs and eis probes tested against clinical DNA with wild type and mutant sequences

| | | Mean Tm (°C.) | | | SD (° C.) for probe no: | | | dTm (° C.) for probe no. | | | No. of isolates detected/Total no. of isolates with the mutation type |
|---|---|---|---|---|---|---|---|---|---|---|---|
| | | rrs-1400 | eis1 | eis2 | 1 | 2 | 3 | 1 | 2 | 3 | |
| | No mutation (NM) | 70.10 | 63.90 | 69.00 | 0.15 | 0.19 | 0.23 | | | | 487/487 |
| rrs gene | A1401G | 66.20 | 63.90 | 69.10 | 0.10 | 0.20 | 0.20 | 3.90 | 0.00 | −0.10 | 75/75 |
| | A1401G + NM | 66.20-70.10 | 64.00 | 69.10 | 0.18 | 0.10 | 0.10 | 3.90 | −0.10 | −0.10 | 3/4 |
| | C1402T + NM | 64.50-70.10 | 64.10 | 69.20 | 0.00 | 0.00 | 0.00 | 5.60 | −0.20 | −0.20 | 1/1 |
| eis promoter | C(−8) deletion | 70.10 | 64.10 | 63.10 | 0.00 | 0.00 | 0.00 | 0.00 | −0.20 | 5.90 | 1/1 |
| | G(−10)A | 70.20 | 63.80 | 64.70 | 0.10 | 0.20 | 0.20 | −0.10 | 0.10 | 4.30 | 14/14 |
| | G(−10)A + NM | 70.20 | 63.80 | 64.80-69.10 | 0.10 | 0.20 | 0.20 | −0.10 | 0.10 | 4.20 | 1/1 |
| | C(−12)T | 70.15 | 64.04 | 62.92 | 0.08 | 0.22 | 0.03 | −0.05 | −0.13 | 6.08 | 2/2 |
| | C(−14)T | 70.10 | 64.00 | 62.60 | 0.10 | 0.20 | 0.20 | 0.00 | −0.10 | 6.40 | 10/10 |
| | G(−37)T | 70.20 | 58.80 | 69.10 | 0.10 | 0.10 | 0.20 | −0.10 | 5.10 | −0.10 | 4/4 |
| rrs gene + eis promoter | rrs-A1401G + eis C(−14)T | 66.30 | 64.10 | 62.50 | 0.12 | 0.14 | 0.17 | 3.80 | −0.20 | 6.50 | 4/4 |

SD represents the +/− standard deviation of the Tm values for each of the probes for the different clinical samples and dTm represents the Tm difference of the mutant sequences from the wild type sequences for each probe.

SD; standard deviation, dTM; delta Tm

Probe no 1, 2 and 3 correspond to rrs-1400, eis-1 and eis-2 probes respectively.

TABLE 4

Susceptibility of the clinical strains to AMK and KAN by the LJ and MGIT methods and their relation to the mutations present in the rrs gene and the eis promoter region

|  | rrs A1401G | rrs C1402T | eis promoter mutations | rrs gene and eis promoter wild type | Total number of isolates |
|---|---|---|---|---|---|
| AMK-Resistant (LJ) | 82 | 0 | 1 | 7 | 90 |
| AMK-Susceptible (LJ) | 0 | 1 | 31 | 481 | 513 |
| KAN-Resistant (LJ) | 82 | 0 | 11 | 13 | 106 |
| KAN-Susceptible (LJ) | 0 | 1 | 21 | 475 | 497 |
| KAN-Resistant (MGIT) | 63 | 0 | 30 | 20 | 113 |
| KAN-Susceptible (MGIT) | 1 | 0 | 1 | 445 | 447 |

LJ and MGIT imply susceptibility testing by the LJ proportions and the MGIT methods respectively.

LJ and MGIT imply susceptibility testing by the LJ proportions and the MGIT methods respectively.

TABLE 5

Susceptibility of the clinical strains to AMK and KAN and mutations in the 5' untranslated region of the whiB7 gene

| Isolate # | Patient # | AMK (LJ) | KAN (LJ) | KAN (MGIT) | whiB7 5' UTR |
|---|---|---|---|---|---|
| #1 | 1 | S | S | R | NM |
| #2 | 2 | S | S | R | NM |
| #3 | 3 | S | S | R | NM |
| #4 | 3 | S | S | R | NM |
| #5 | 4 | S | R | R | NM |
| #6 | 5 | S | R | R | +273-A -> C |
| #7 | 5 | S | R | ND | +273-A -> C |
| #8 | 5 | S | R | R | +273-A -> C |
| #9 | 6 | R | R | R | NM |
| #10 | 6 | S | S | R | NM |
| #11 | 6 | R | R | ND | NM |
| #12 | 7 | S | S | R | +138-C deletion |
| #13 | 8 | S | S | R | NM |
| #14 | 9 | S | S | R | Probable deletion in UTR |
| #15 | 9 | S | S | R | Probable deletion in UTR |
| #16 | 9 | S | S | R | Probable deletion in UTR |
| #17 | 10 | R | R | R | NM |
| #18 | 11 | S | S | R | NM |
| #19 | 12 | R | R | S | NM |
| #20 | 13 | S | R | R | +237-A -> G |
| #21 | 13 | S | R | R | +237-A -> G |
| #22 | 14 | R | R | R | NM |

LJ and MGIT imply susceptibility testing by the LJ proportions and the MGIT methods respectively.

ND; not determined, NM; no mutation, R; resistant, S; susceptible.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. An oligonucleotide set for amplifying a portion of a *Mycobacterium tuberculosis* katG gene, comprising,
   a pair of forward and reverse primers specific for said portion, wherein the forward primer comprises the sequence of SEQ ID NO: 7, 8, or 9 and the reverse primer comprises the sequence of SEQ ID NO: 10 or 11 and
   an isolated nucleic acid probe consisting of the sequence of SEQ ID NO: 56, wherein the nucleic acid probe is labeled with a fluorophore and a quencher at its two ends respectively.

2. The oligonucleotide set of claim 1, wherein the fluorophore is fluorescein, cyanine 5, TexasRed or TAMRA and wherein the quencher is BHQ1, BHQ2, or DABCYL.

3. An isolated nucleic acid probe consisting of the sequence of SEQ ID NO: 56 wherein the nucleic acid probe is labeled with a fluorophore and a quencher at its two ends respectively.

4. The nucleic acid probe of claim 3, wherein the fluorophore is fluorescein, cyanine 5, TexasRed or TAMRA and wherein the quencher is BHQ1, BHQ2, or DABCYL.

5. A kit comprising an oligonucleotide set or nucleic acid probe of any one of claims 1 and 3, a DNA polymerase, extension nucleotides, and a buffer.

6. A method for detecting presence of *Mycobacterium tuberculosis* in a test sample, comprising contacting the test sample with a pair of forward and reverse primers specific for a portion of a katG gene, wherein the forward primer comprising the sequence of SEQ ID No: 7, 8, or 9 and the reverse primer comprises the sequence of SEQ ID No: 10 or 11, under conditions conductive to amplifying reaction to yield a first amplicon, hybridizing the first amplicon with a probe consisting of the sequence of SEQ ID No: 56, and detecting *Mycobacterium tuberculosis* based upon the hybridization.

7. The method of claim 6, further comprising
   contacting the test sample with a second primer pair under conditions conducive to an amplifying reaction to yield a second amplicon, and
   detecting the presence of said second amplicon,
   whereby presence of both the first amplicon and second amplicon indicates the presence of *Mycobacterium tuberculosis* in said test sample.

8. A method for detecting presence of *Mycobacterium tuberculosis* in a test sample, comprising contacting the test sample with a pair of forward and reverse primers specific for a portion of a katG gene, wherein the forward primer comprising the sequence of SEQ ID No: 7, 8, or 9 and the reverse primer comprises the sequence of SEQ ID No: 10 or 11, under conditions conductive to amplifying reaction to yield a first amplicon, hybridizing the first amplicon with a molecular beacon probe consisting of the sequence of SEQ ID No: 56 and labels of a fluorophore and a quencher at the two ends of the sequence, and detecting *Mycobacterium tuberculosis* based upon the hybridization.

\* \* \* \* \*

UNITED STATES PATENT AND TRADEMARK OFFICE
CERTIFICATE OF CORRECTION

Page 1 of 1

PATENT NO. : 11,180,816 B2
APPLICATION NO. : 15/517042
DATED : November 23, 2021
INVENTOR(S) : David Alland It is certified that error appears in the above-identified patent and that said Letters Patent is hereby corrected as shown below:

In the Specification

At Column 1, Line number 14 should read:
STATEMENT REGARDING FEDERALLY SPONSORED RESEARCH
This invention was made with government support under grant numbers AI080653, AI082174 awarded by the National Institutes of Health. The government has certain rights in the invention.

Signed and Sealed this
Sixteenth Day of April, 2024

Katherine Kelly Vidal
*Director of the United States Patent and Trademark Office*